(12) United States Patent
Al Muderis

(10) Patent No.: US 10,456,178 B2
(45) Date of Patent: Oct. 29, 2019

(54) OSSEOINTEGRABLE DEVICE

(71) Applicant: Osseointegration Holdings Pty Ltd, McMahons Point, New South Wales (AU)

(72) Inventor: Munjed Al Muderis, Milsons Point (AU)

(73) Assignee: OSSEOINTEGRATION HOLDINGS PTY LTD, McMahons Point (AU)

( * ) Notice: Subject to any disclaimer, the term of this patent is extended or adjusted under 35 U.S.C. 154(b) by 60 days.

(21) Appl. No.: 15/110,608

(22) PCT Filed: Apr. 16, 2015

(86) PCT No.: PCT/AU2015/000234
§ 371 (c)(1),
(2) Date: Jul. 8, 2016

(87) PCT Pub. No.: WO2015/157809
PCT Pub. Date: Oct. 22, 2015

(65) Prior Publication Data
US 2016/0331422 A1    Nov. 17, 2016

(30) Foreign Application Priority Data

Apr. 16, 2014 (AU) ................ 2014901404
May 23, 2014 (AU) ................ 2014901958
Jun. 20, 2014 (AU) ................ 2014902373

(51) Int. Cl.
*A61B 17/72* (2006.01)
*A61F 2/78* (2006.01)

(52) U.S. Cl.
CPC ...... *A61B 17/7283* (2013.01); *A61B 17/7233* (2013.01); *A61F 2/78* (2013.01); *A61F 2002/7887* (2013.01)

(58) Field of Classification Search
CPC .. A61B 17/7233; A61B 17/7283; A61B 17/72
See application file for complete search history.

(56) References Cited

U.S. PATENT DOCUMENTS 4,158,895 A      6/1979  Frosch et al.
4,976,258 A  *  12/1990  Richter .................. A61B 17/72
                                                                606/64

(Continued)

FOREIGN PATENT DOCUMENTS

DE           3439993 A1    5/1986
DE     102009027255 A1    8/2010

(Continued)

OTHER PUBLICATIONS

Holt, B. M., et al. "Immediate post-implantation skin immobilization decreases skin regression around percutaneous osseointegrated prosthetic implant systems", Journal of Biomedical Materials Research, Part A, Jul. 2013, vol. 101A, issue 7, pp. 2075-2082.

(Continued)

*Primary Examiner* — Julianna N Harvey
(74) *Attorney, Agent, or Firm* — Harness, Dickey & Pierce, P.L.C.

(57) ABSTRACT

An implant arranged for integration into a skeletal bone of a patient, comprising: a body having at least one end, the body being arranged to substantially mimic a portion of a skeletal bone; wherein the at least one end includes an enlarged portion arranged to, in use, prevent migration of the implant into the flesh of a patient.

20 Claims, 25 Drawing Sheets

(56) References Cited

U.S. PATENT DOCUMENTS

| | | | | |
|---|---|---|---|---|
| 5,169,597 A | * | 12/1992 | Davidson | A61B 17/72 148/316 |
| 2010/0331996 A1 | | 12/2010 | Blunn et al. | |
| 2014/0156022 A1 | | 6/2014 | Holt et al. | |
| 2014/0195002 A1 | | 7/2014 | Bachus et al. | |

FOREIGN PATENT DOCUMENTS

| | | |
|---|---|---|
| GB | 2507327 A | 4/2014 |
| WO | WO-2014040061 A1 | 3/2014 |
| WO | WO-2014063816 A1 | 5/2014 |

OTHER PUBLICATIONS

Pendegrass, C. J., et al. "Development of a soft tissue seal around bone-anchored transcutaneous amputation prostheses" Biomaterials 2006, vol. 27, pp. 4183-4191.
International Search Report and Written Opinion of the International Searching Authority for PCT/AU2015/000234, dated May 27, 2015; ISA/AU.
Demand for IPE and Response to Written Opinion (dated Feb. 15, 2016).
Written Opinion of the International Preliminary Examining Authority for PCT/AU2015/000234, dated Mar. 3, 2016; IPEA/AU.
Response to Second Written Opinion (dated Apr. 6, 2016).
Second Written Opinion of the International Preliminary Examining Authority for PCT/AU2015/000234, dated May 10, 2016; IPEA/AU.

\* cited by examiner

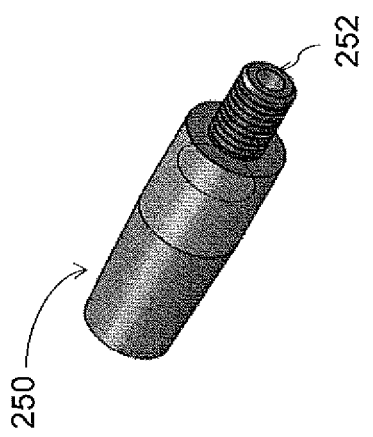
Figure 5B
Figure 5C
Figure 5A

OSSEOINTEGRABLE DEVICE

TECHNICAL FIELD

The present invention relates to a device for osseointegration into a patient. Embodiments of the invention find specific, but not exclusive, use in the provision of an osseointegrable component arranged to fit and integrate with a portion of a missing femoral or tibial bone in the leg of a patient. However, it will be understood that the invention has broader application.

BACKGROUND ART

The following discussion of the background art is intended to facilitate an understanding of the present invention only. The discussion is not an acknowledgement or admission that any of the material referred to is or was part of the common general knowledge as at the priority date of the application.

Osseointegration is a technique which provides amputee patients with a prosthetic implant which is integrated with the skeleton of a patient. That is, an implant where there is direct contact between living bone and the surface of a load bearing implant. Osseointegration dramatically enhances bone and joint replacement surgery by providing much stronger and longer lasting implants, which in turn provides greater quality of life for amputees.

In some currently utilised osseointegration implants, a skeletally integrated implant is connected through an opening in the stump of an amputee to an external prosthetic limb. This allows direct contact to the ground, which provides greater stability, more control and minimizes energy exerted.

As there is a direct connection between the implant and the external prosthetic limb, there is no need for a patient to use a so-called "suction" prosthesis. Patients that are unable to wear a suction prosthesis for long periods of time or those confined to a wheel chair may benefit from osseointegration implants. Indeed, bilateral amputees have been able to become mobile through osseointegration.

In some other currently utilised osseointegration implants, such as for example the implants the subject of US 2014/0195002 and US 2014/0156022, part of the implant form an abutment against the cut bone with portions of the implant extending beyond outside the cut bone. In these circumstances an implant-abutment interface is formed by against the cut bone. In such a high stress region, this implant-abutment inevitably creates small gaps between the implant and the bone. These small gaps present regions within which bacteria may colonise, potentially causing inflammation and infection.

In the other currently utilised osseointegration implants mentioned above with reference to US 2014/0195002 and US 2014/0156022 there is a region of the implant extending outwardly from the implant-abutment that interfaces with the patient's soft tissue causing friction between the soft tissue and implant.

It is against this background that embodiments of the present invention have been developed.

SUMMARY OF INVENTION

In a first aspect, the present invention provides an implant arranged for integration into a skeletal bone of a patient, comprising a body and at least one end, the body being arranged to sit within a passageway formed within the bone and substantially mimic a portion of a skeletal bone, wherein the at least one end includes an enlarged portion arranged to, in use, prevent migration of the implant into the skeletal bone of a patient, wherein the enlarged portion is arranged to sit within a recess formed in an end of the skeletal bone, and wherein the recess is connected to the passageway and is of a larger diameter of the passageway.

The width of the enlarged portion may be narrower than the width of the skeletal bone so that the enlarged portion sits entirely within the recess formed in an end of the skeletal bone.

The at least one end may include the enlarged portion is arranged so that the end is flush with the end of the skeletal bone.

The enlarged portion may be tapered away from the body.

The enlarge portion may be flared away from the body.

The skeletal bone may be a femur.

The skeletal bone may be a tibia.

The enlarged portion may be a formed through flaring of the enlarged portion.

The enlarged portion may be formed by the enlarged portion being stepped with stepped with respect to the body.

The width of at least a portion of the enlarged portion may be greater than the width of the body.

The at least one end may be arranged to sit within the skeletal bone.

The at least one end may be arranged to sit within a recess formed within the skeletal bone.

The enlarged portion may include a coupling portion arranged to, in use, receive a coupling part.

The coupling portion may further comprise a locking pin.

The locking pin may be tapered.

The body may include a coating arranged to assist osseointegration of the implant into the skeletal bone. In one embodiment, the coating includes a porous structure arranged to assist osseointegration of the implant into the existing skeletal bone. The porous structure may be formed from titanium, which may in turn be formed by a plasma deposition process.

The implant may be sized to replace at least a portion of a human femoral bone. The implant may also have a curved shape, arranged to mimic the curve of a human femoral bone.

In one embodiment, the body of the implant further includes at least one projection which extends along a portion of the body, wherein the projection is arranged to, in use, prevent rotation of the implant relative to the skeletal bone. The projection may be at least one spline. The at least one spline may extend longitudinally along the body of the implant.

The implant may have a second end.

The second end may be tapered.

The second end may include a second coupling portion.

A portion of the at least one end of the implant may be coated with a physiologically inert substance. The physiologically inert substance may be niobium.

The coupling part may include a threaded portion arranged to receive a corresponding coupling portion on a prosthetic device.

The implant may include a plurality of splines, wherein a recessed channel is located between adjacent splines.

In another aspect, the present invention provides a method of surgically implanting an implant into a skeletal bone of a patient, the method comprising the steps of forming a longitudinal cavity in the bone of the patient, the cavity being arranged to, in use, receive the implant, wherein the cavity comprises at least one end wherein the at least one end of the cavity further comprises a stepped portion formed to substantially mimic the shape of the implant, and implanting the implant into the cavity.

In yet another aspect, the present invention provides a method of surgically preparing a skeletal bone of a patient for receiving an implant, the method comprising the step of forming a longitudinal cavity in the bone of the patient, the cavity comprising at least one end, the cavity arranged to, in use, receive the implant, wherein the at least one end of the cavity further comprises a stepped portion formed to substantially mimic the shape of the implant.

The body may include an aperture distal to the enlarged portion arranged to receive a locking means arranged to fix the body to the skeletal bone.

The body of the implant may be of a generally triangular profile.

In yet a further aspect, the present invention provides an implant arranged for integration into a skeletal bone of a patient, comprising a body and at least one end, the body being arranged to sit within a passageway formed within the bone and substantially mimic a portion of a skeletal bone, wherein the at least one end includes an enlarged portion arranged to, in use, prevent migration of the implant into the patient, wherein the body includes an aperture distal to the enlarged portion arranged to receive a locking means arranged to fix the body to the skeletal bone.

The aperture may be a passageway that passes through the body of the implant.

The locking means may be a rod.

The locking means may be a screw.

BRIEF DESCRIPTION OF THE DRAWINGS

Further features of the present invention are more fully described in the following description of several non-limiting embodiments thereof. This description is included solely for the purposes of exemplifying the present invention. It should not be understood as a restriction on the broad summary, disclosure or description of the invention as set out above. The description will be made with reference to the accompanying drawings in which:

FIGS. 5A to 5C are front, side and projected views of a first coupling member arranged to couple with the osseointegrative implant in accordance with an embodiment of the invention;

DESCRIPTION OF EMBODIMENTS

Figure 1:
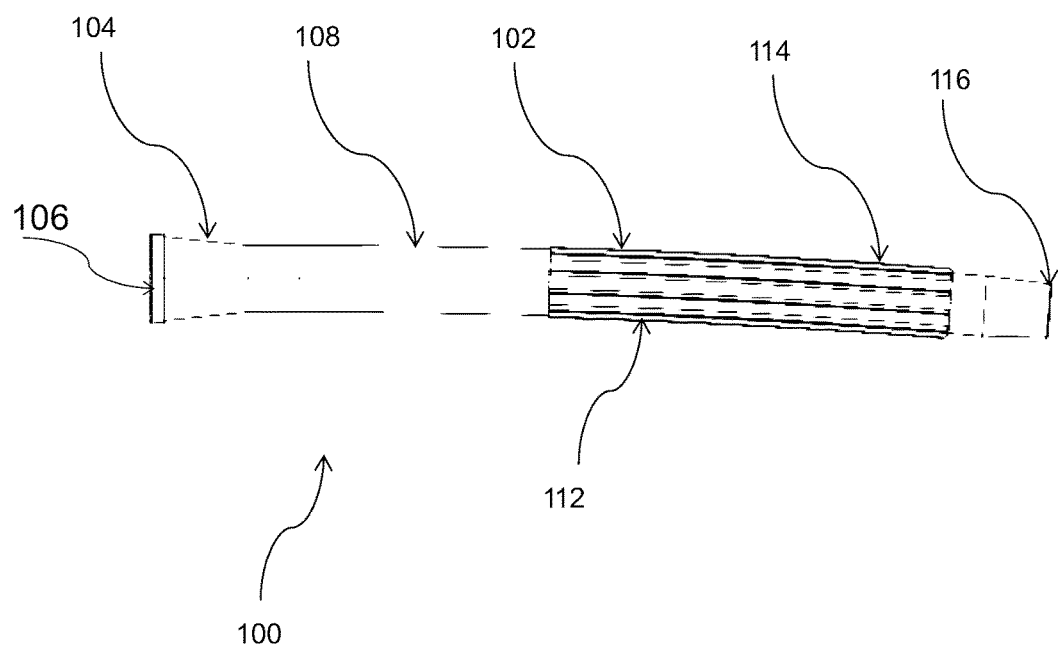
FIGS. 1 and 2 are side views of an osseointegrative implant in accordance with an embodiment of the present invention.
Figure 2:
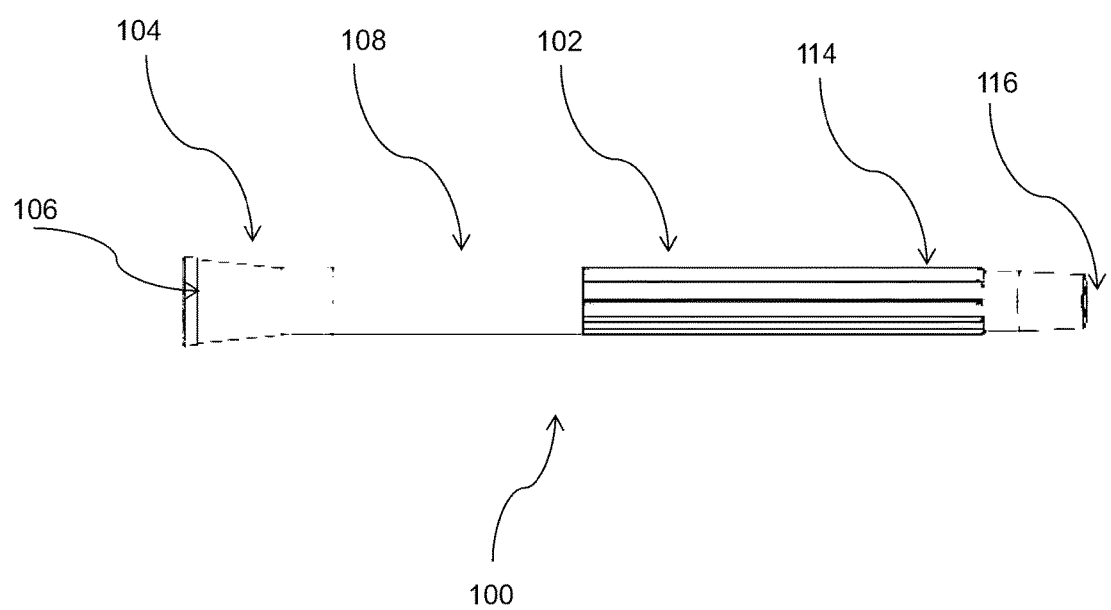
Figure 3:
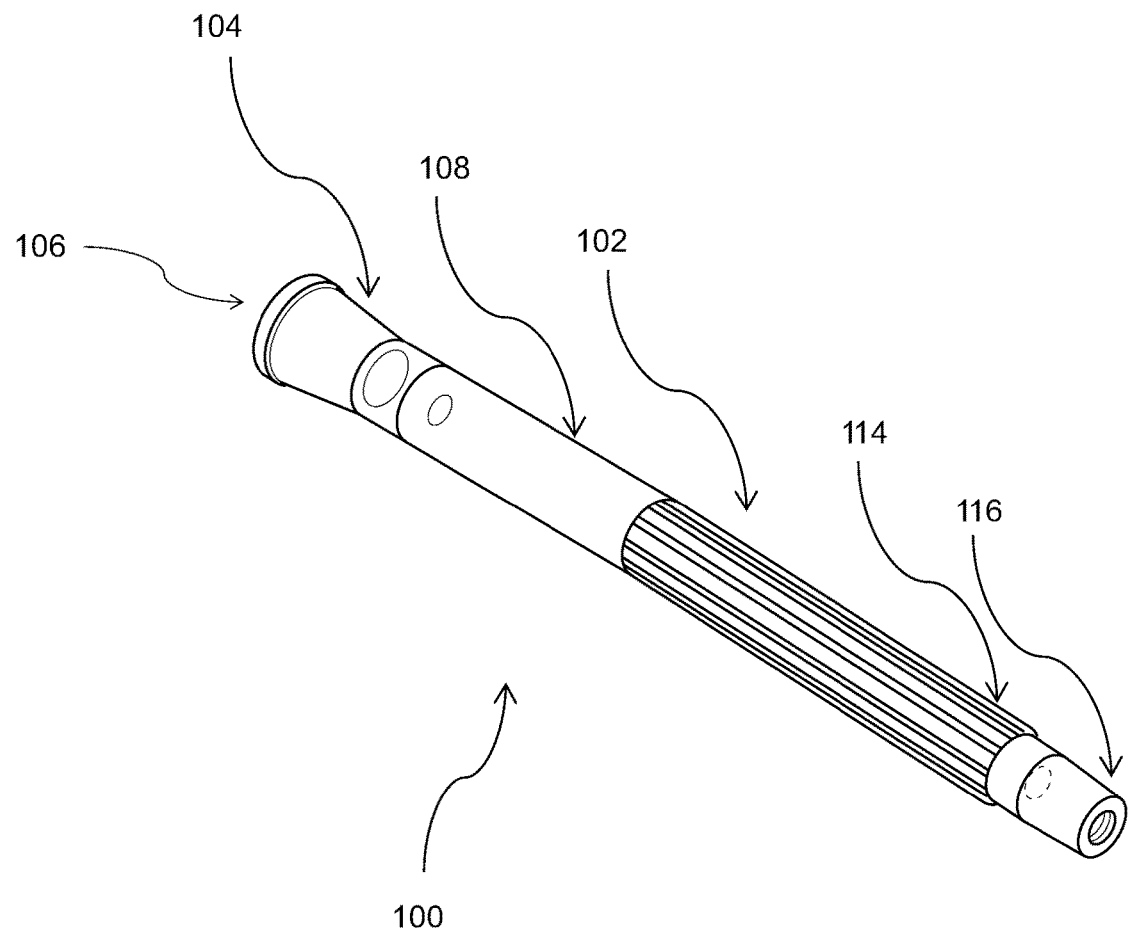
FIG. 3 is a projected view of an osseointegrative implant in accordance with an embodiment of the present invention.

Broadly, embodiments of the present invention relate to an implant arranged for integration into an existing skeletal bone of a patient. Such implants are generally referred to as "osseointegrative" implants. The implants of the present invention are particularly suited for implantation into long bones such as the femur, tibia or humerus.

In the ensuing description, like reference numerals in consecutive Figures refer to like or functionally identical parts.

The embodiment described herein, with reference to FIGS. 1 through 4, include an implant 100 with a body 102 having a distal end 104. The implant 100 is well suited for integration into a femur. This does not suggest that the implant 100 is solely suitable for use with a femur.

In one arrangement the implant 100 is forged titanium chosen for its biocompatibility. The skilled addressee will recognize that alternative materials that are biocompatible can be used such as titanium alloys, composite materials or otherwise.

The body 102 is elongate as it is arranged to substantially mimic a portion of a skeletal bone. In the embodiment described herein, the implant 100 is designed to be implanted in the leg of a patient, as a partial replacement for the femur bone of a patient. The patient is an amputee who is seeking to use a prosthetic limb and requires the implant to serve as an "attachment" point for the prosthetic limb.

The distal end 104 which includes a flared portion 106, that is enlarged with respect to the body 102, arranged to, in use, prevent migration of the implant into the flesh of a patient. Osseointegrative implants suffer from the issue of the 'end' of the implant, which is necessarily open to the air and passes through the flesh and skin of a patient, being slowly 'pushed upwards' (i.e. upwardly migrating) when the patient wears a prosthetic limb which exerts upward pressure on the implant and therefore can cause the end of the implant to migrate into the flesh of the leg of the patient. The embodiment described herein, in contrast, utilizes a flared portion 106 to prevent such 'upward migration' of the implant into the leg of the patient.

The flared portion 106 is sized and shaped to sit within a recess 155 formed in the exposed end 157 of the bone 110. As a result of this the flared portion 106 has a perimeter that is smaller than that of the skeletal bone it is to be inserted into. The recess 155 is shaped so that the end of the flared portion 106 is flush with the end of the bone 110.

As the flared portion 106 is flush with the end of the bone 110 after the implant is inserted, a surgeon can suture the skin to the outside of the bone surrounding the implant. As the flared portion 106 does not extend beyond the end of the bone 110 no site is presented for a bacteria colony to develop. This greatly reduces the risk of inflammation, infection and destruction of tissue around the implant site due to bacterial activity.

Also, as the flared portion 106 is flush with the end of the bone 110 after the implant is inserted, the soft tissue surrounding the bone 110 does not adhere to the implant. As a result forces transmitted through the implant 100, such as through walking or otherwise, are directly transferred through the implant 100 and bone 110 and are not dissipated either through a socket or through soft tissue. This minimizes energy loss.

In one embodiment, the end of the flared portion 106 is coated with nano particles or is highly polished to minimize the friction between the soft tissue surrounding the implant and resultant irritation felt by the patient.

As soft tissue dues not adhere to the implant 100, muscles and soft tissue surrounding the implant 106 and bone is encouraged to adhere to the bone in a natural fashion. This minimizes or eliminates muscle wastage and allows the patient to feel the sensory interactions of walking or otherwise that would otherwise be lost.

The flared portion 106 is enlarged with respect to the body portion 102 so that the flared portion is wider than the body portion 102. This results in the flared portion 106 having a larger cross sectional area that the body portion 102.

At least part of the flared portion 106 is covered by a physiologically inert substance, to reduce the possibility of infection or an immune reaction at the site at which the implant 100 protrudes from the stump of a patient's leg. In the embodiment described herein, the physiologically inert substance is niobium, but it will be understood that other coatings may be used, such as gold, or any other coating known or discovered to be physiologically inert. Such variations are within the purview of a person skilled in the art.

Figure 4:
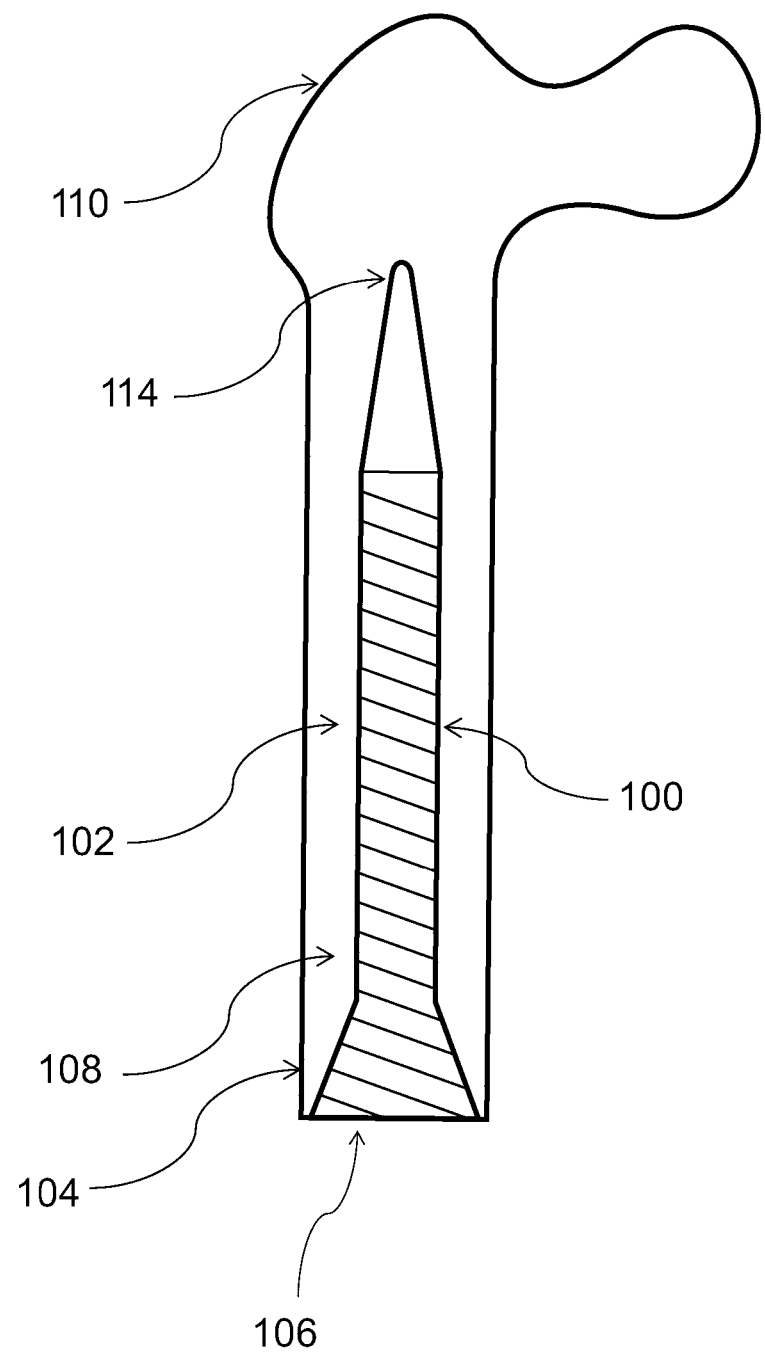
FIG. 4 is aside view of an osseointegrative implant in accordance with an embodiment of the present invention, when implanted in a femur bone.
Figure 6A:
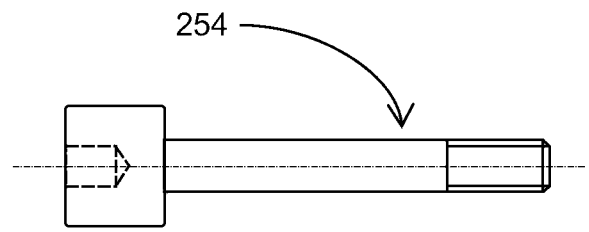
FIGS. 6A to 6C are front side and projected views of a second coupling member arranged to couple with the first coupling member of FIGS. 5A to 5C.
Figure 6B:
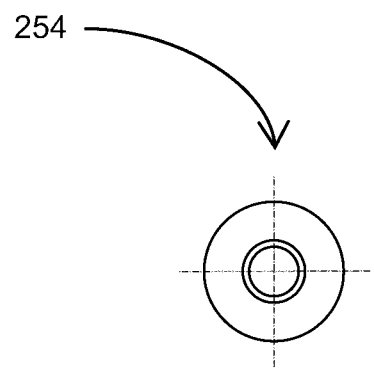
Figure 6C:
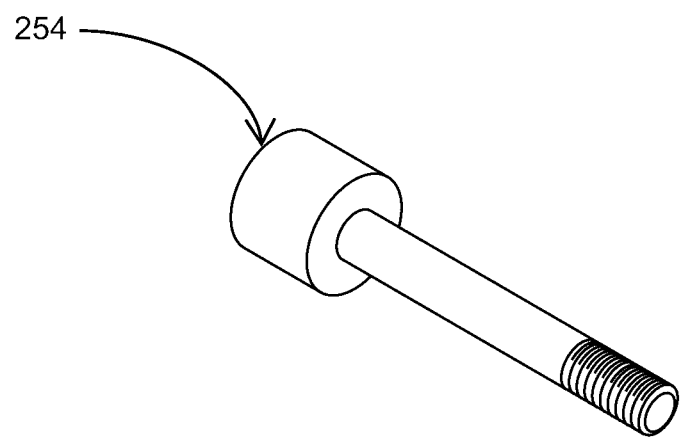
Figure 12:
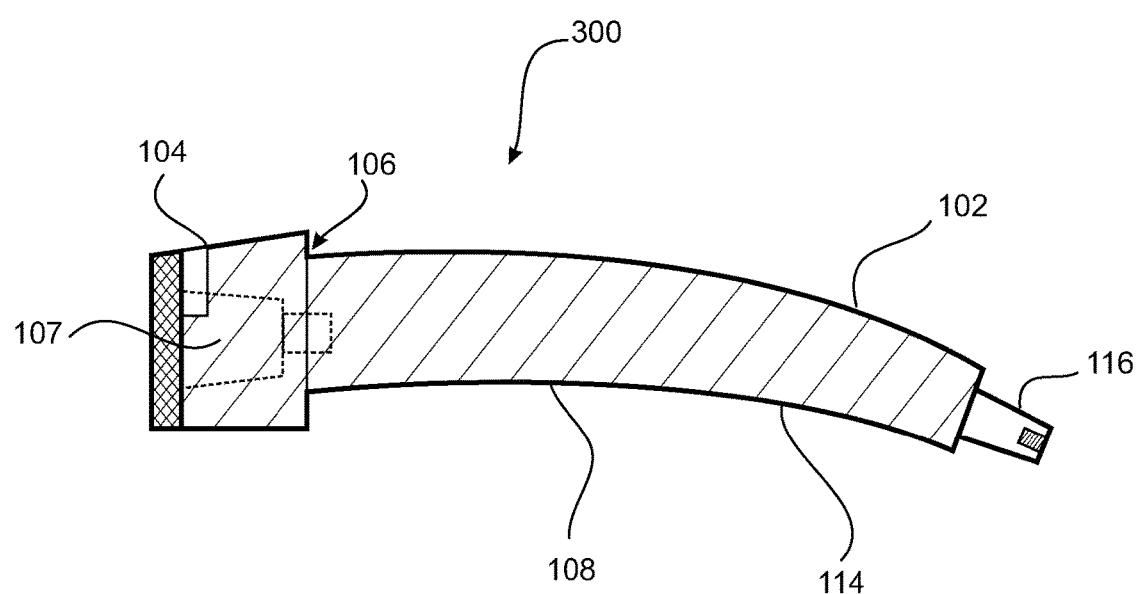
FIG. 12 is a side view of an osseointegrative implant in accordance with a third embodiment of the present invention.
Figure 15A:
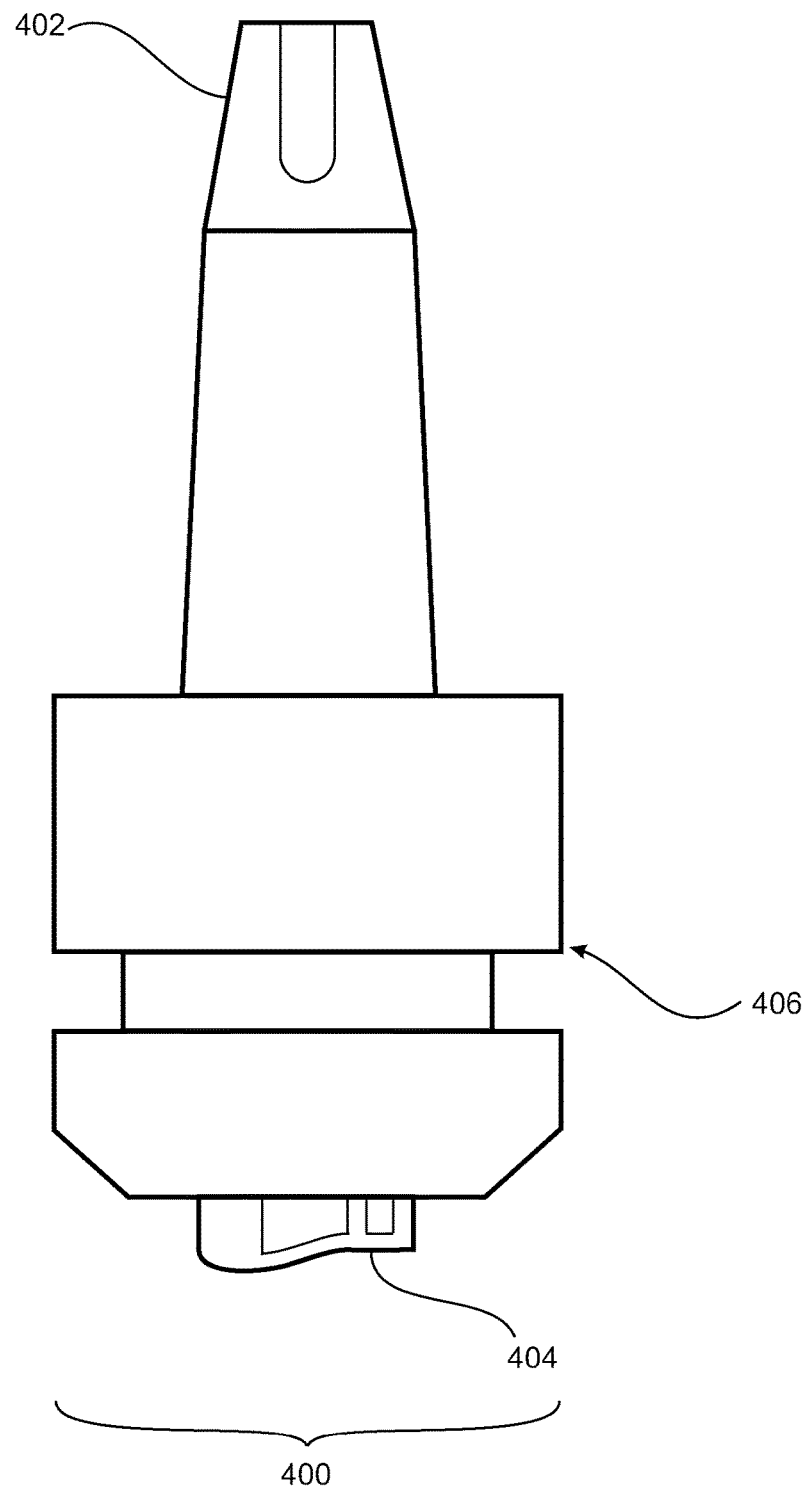
FIGS. 15A and 15C are front and projected views of a first coupling part arranged to couple at one end with the osseointegrative implant of FIG. 12.
Figure 15B:
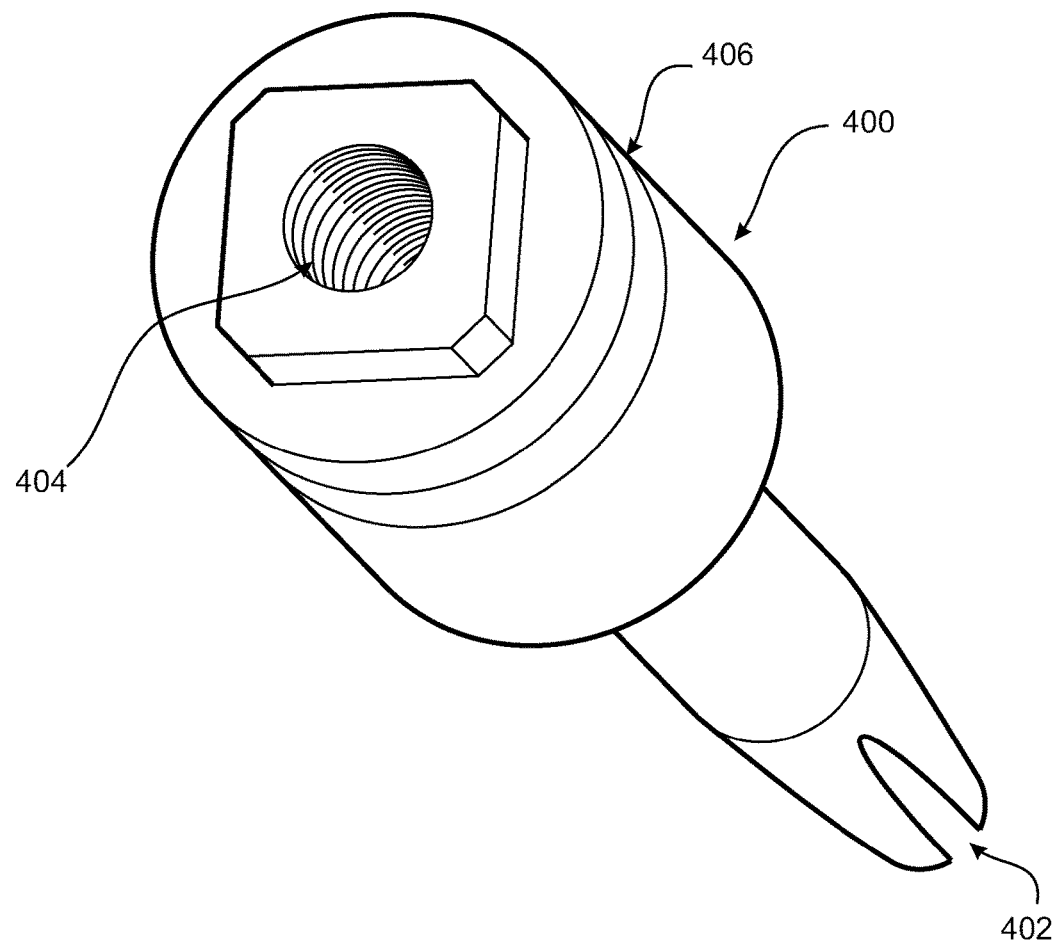

FIGS. 15A and 15B are front, and projected views of a first coupling part arranged to couple at one end with the osseointegrative implant of FIG. 12;

In addition to the flared portion 106 having a coating, at least a portion of the body 102 may also have a coating (generally denoted by 108), which has the purpose of assisting the implant 100 to integrate into the existing skeletal bone (shown as 110 in FIG. 4).

In one embodiment, the coating is a suitable porous structure which assists in encouraging bone growth into the porous structure, thereby assisting osseointegation of the implant into the existing skeletal bone. In one embodiment, the porous structure is formed from titanium which is deposited on the surface of the body 102 by using a plasma deposition process.

The implant has a curved shape which is generally visible at area 112, which is arranged to mimic the curve of a human femoral bone. It will be understood that different types of implants may have different shapes and profiles, as may be required to meet certain physiological constraints. Such variations are within the purview of a person skilled in the art.

The body 102 of the implant 100 further includes at least one projection 114 which extends along a portion of the body 102. The projection is arranged to, in use, prevent rotation of the implant relative to the skeletal bone, by providing 'grip' to prevent rotation of the implant 100 when it is located inside the skeletal bone. In the embodiment shown in the Figures, the projection 114 is at least one spline which extends longitudinally along the body of the implant. However, it will be understood that other variations which achieve the same functionality may include the provision of raised patterns (a 'zig-zag' pattern), circumferential ridges, or other simple or complex patterns.

The implant 100 also has a proximal end 116 which is tapered, to allow the patient to also receive an artificial hip implant (or other implant).

In one arrangement, the at least one projection 114 is located in the region adjacent the proximal end 116. The porous portion 108 for bio adhesion is located adjacent the distal end 104.

Referring now to FIGS. 5A to 5C and 6A to 6C there is shown a first coupling part 250 which includes a threaded portion 252 arranged to receive a corresponding coupling portion 254 which connects to a prosthetic device (not shown).

In a second embodiment described herein, with reference to FIGS. 7 through 11, an implant 200 which comprises a body 202 having at least one end 204. The body 202 is elongate as it is arranged to substantially mimic a portion of a skeletal bone and in the example embodiment described herein, the implant is arranged to mimic at least a portion of a tibia bone of a human patient. This does not suggest that the implant 200 is solely suitable for use with a tibia.

Implant 200 can be formed through 3D printing or by other means as understood by the skilled addressee and is made of a biocompatible material.

As the implant 200 is arranged to mimic a portion of a tibia bone it has a generally triangular cross sectional profile to suite the cross sectional profile of a tibia. The skilled addressee will recognize that variations.

The distal end 204 which includes a flared portion 206 arranged to, in use, prevent migration of the implant into the bone of a patient. Osseointegrative implants suffer from the issue of the 'end' of the implant, which is necessarily open to the air and passes through the flesh and skin of a patient, being slowly 'pushed upwards' (i.e. upwardly migrating) when the patient wears a prosthetic limb which exerts upward pressure on the implant and therefore can cause the end of the implant to migrate into the bone of the leg of the patient. The embodiment described herein, in contrast, utilises a flared portion 206 to spread the upward pressure on the bone and thereby prevent such 'upward migration' of the implant into the leg of the patient.

Figure 11:
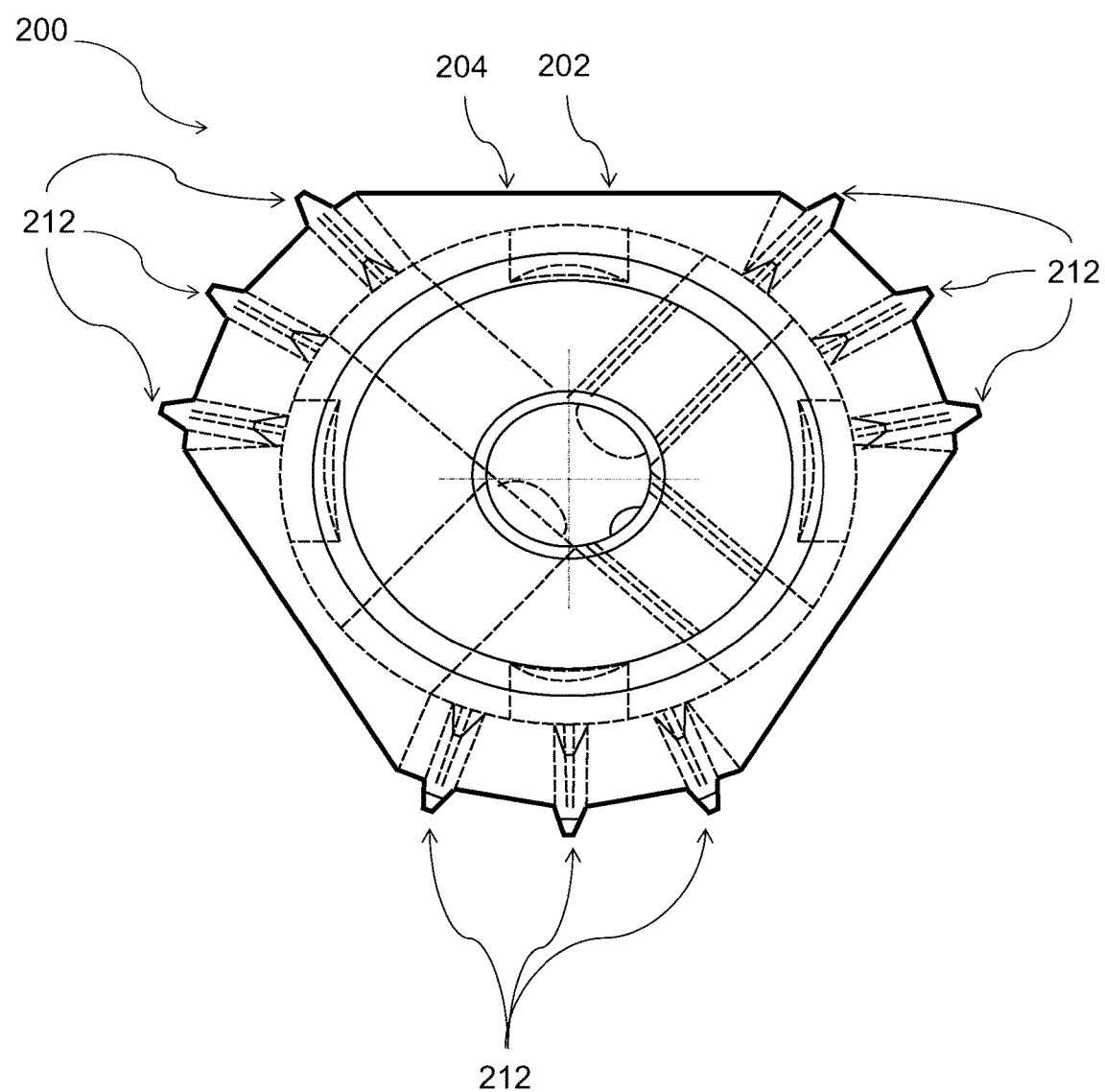
FIG. 11 is a side view of the implant device of FIG. 7.

It will also be understood that the flared portion 206 of the implant has a substantially triangular cross-section (i.e. in the embodiment shown, three substantially straight walls, which are connected by rounded corners, as shown in FIG. 11). However, it will be noted that the body 202 has a substantially round (circular) cross section. That is, the implant 200 converges from being substantially triangular at the distal end 204 to being substantially round at the body 202.

At least part of the body 202 is covered with a rough coating which assists in the osseointegration of the body 202 into the bone of a patient. In one embodiment, the coating is a suitable porous structure which assists in encouraging bone growth into the porous structure, thereby assisting osseointegration of the implant into the skeletal bone. In one embodiment, the porous structure is formed from titanium which is deposited on the surface of the body 202 by using a plasma deposition process.

The flared portion 206 is sized and shaped to sit within a recess formed in the exposed end of the bone. As a result of this the flared portion 206 has a perimeter that is smaller than that of the skeletal bone it is to be inserted into. The recess is shaped so that the end of the flared portion 206 is flush with the end of the bone.

As the flared portion 206 is flush with the end of the bone after the implant is inserted, a surgeon can suture the skin to the outside of the bone surrounding the implant. As the flared portion 106 does not extend beyond the end of the bone no site is presented for a bacteria colony to develop. This greatly reduces the risk of inflammation, infection and destruction of tissue around the implant site due to bacterial activity.

Also, as the flared portion 206 is flush with the end of the bone after the implant is inserted, the soft tissue surrounding the bone does not adhere to the implant. As a result forces transmitted through the implant 200, such as through walking or otherwise, are directly transferred through the implant 200 and bone and are not dissipated either through a socket or through soft tissue. This minimizes energy loss.

The end of the flared portion 206 is coated with nano particles or is highly polished to minimize the friction between the soft tissue surrounding the implant and resultant irritation felt by the patient.

As soft tissue dues not adhere to the implant 200, muscles and soft tissue surrounding the implant 206 and bone is encouraged to adhere to the bone in a natural fashion. This minimizes or eliminates muscle wastage and allows the patient to feel the sensory interactions of walking or otherwise that would otherwise be lost.

The flared portion 206 is enlarged with respect to the body portion 202 so that the flared portion is wider than the body portion 202. This results in the flared portion 106 having a larger cross sectional area that the body portion 202.

The distal end 204 of the implant 200 further includes a coupling part 207 which is arranged to receive a coupling portion.

The body 202 of the implant 200 further includes at least one projection 212 adjacent the distal end 204 which extends along a portion of the body 202. The projection is arranged to, in use, prevent rotation of the implant relative to the skeletal bone, by providing 'grip' to prevent rotation of the implant 200 when it is located inside the skeletal bone. In the embodiment shown in the Figures, the projection 214 is at least one spline which extends longitudinally along the body of the implant. However, it will be understood that other variations which achieve the same functionality may include the provision of raised patterns (a 'zig zag' pattern), circumferential ridges, or other simple or complex patterns.

The implant further includes at least one fixing point 214 which in the embodiment are described as 'screw holes', which are arranged to provide one or more fixing points to allow the implant to be fixed to a tibia bone through the use of appropriate screws or other fixing devices.

In one arrangement, the body 202 includes a central bore 299. Screws can be placed in the fixing point 214 through the central bore and then screwed into the surrounding bone when the implant 200 is in place.

It will be understood that the fixing point 214 may be in the form of a threaded bushing. Where the fixing point 214 is a threaded bushing, screws can be partially inserted through the fixing point 214 before the implant 200 is inserted into the bone. When the implant 200 is inserted into the bone the partially inserted screws can be screwed through the central bore fully and engaged with the bone.

In an alternative arrangement, a jig can be placed over the outside of the bone to locate the fixing point 214 and screws can be inserted through the fixing point 214 from outside the bone.

The implant 200 also has a proximal end 216 which includes a second attachment point.

The implant of FIGS. 1 to 6c may include one or more fixing points similar to those of fixing point 214.

Figure 13:
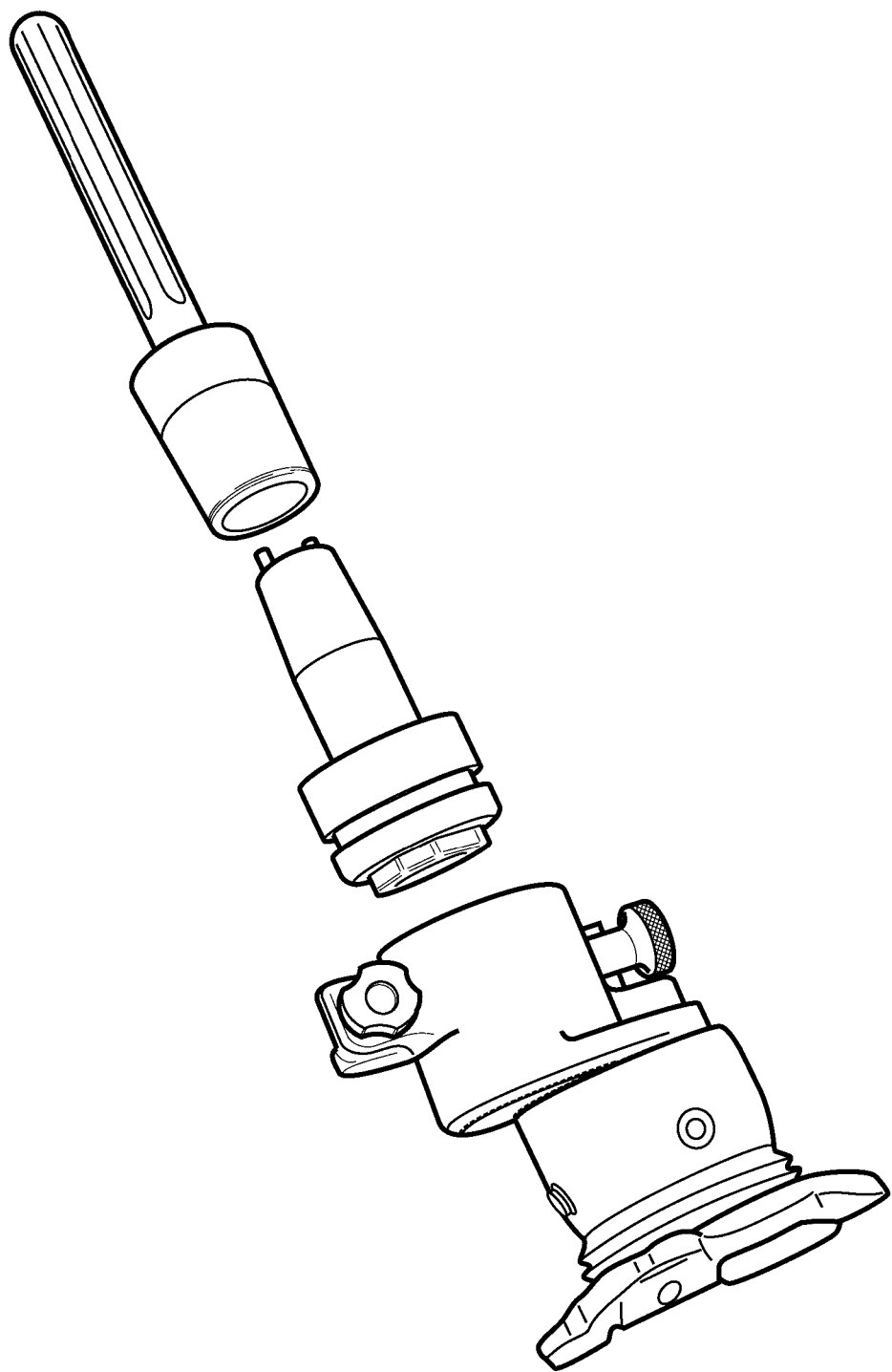
FIG. 13 is a projected view of the osseointegrative implant of FIG. 12.
Figure 14:
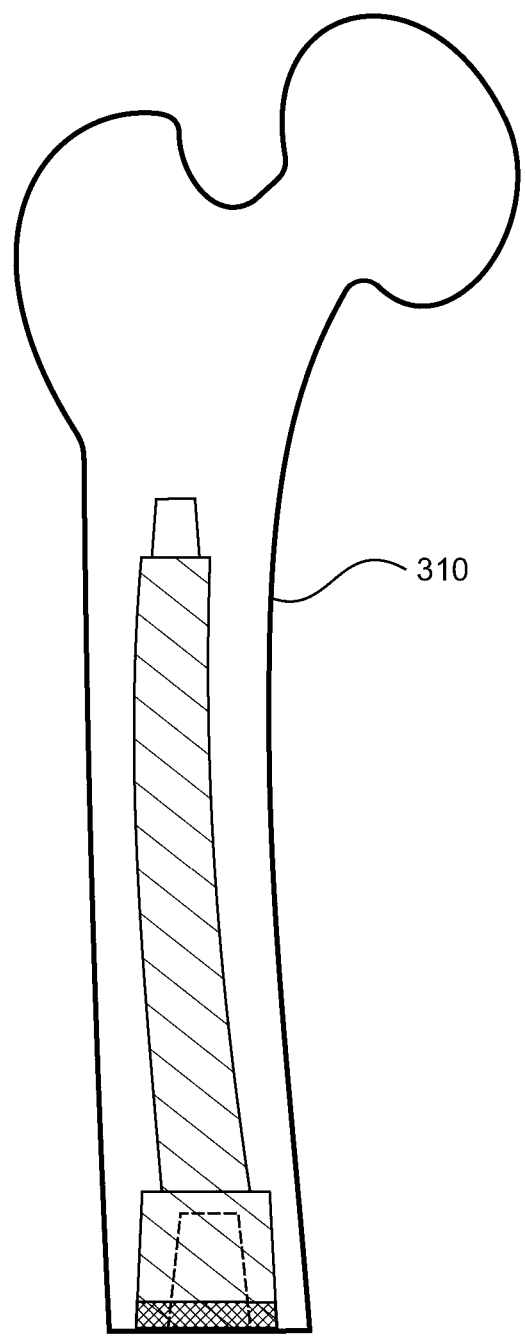
FIG. 14 is a side view of the osseointegrative implant of FIG. 12.

In a third embodiment described herein, with reference to FIGS. 12 through 14, an implant 300 which comprises a body 302 having at least one end 304. The body 302 is elongate as it is arranged to substantially mimic a portion of a skeletal bone. In the embodiment described herein, the implant 300 is designed to be implanted in the leg of a patient, as a partial replacement for the femur bone of a patient. The patient is an amputee who is seeking to use a prosthetic limb and requires the implant to serve as an "attachment" point for the prosthetic limb.

The at least one end 304 which includes a stepped portion 306 arranged to, in use, prevent migration of the implant into the bone of a patient. Osseointegrative implants suffer from the issue of the 'end' of the implant, which is necessarily open to the air and passes through the flesh and skin of a patient, being slowly 'pushed upwards' (i.e. upwardly migrating) when the patient wears a prosthetic limb which exerts upward pressure on the implant and therefore can cause the end of the implant to migrate into the bone of the leg of the patient. The embodiment described herein, in contrast, utilizes a stepped portion 306 to prevent such 'upward migration' of the implant into the leg of the patient.

At least part of the stepped portion 306 is covered by a physiologically inert substance, to reduce the possibility of infection or an immune reaction at the site at which the implant 300 contacts the flesh of the patient's leg. In the embodiment described herein, the physiologically inert substance is niobium, but it will be understood that other coatings may be used, such as gold, or any other coating known or discovered to be physiologically inert. Such variations are within the purview of a person skilled in the art.

The at least one end 304 of the implant 300 further includes a coupling part 307 which is arranged to receive a coupling portion (which will be described in more detail later).

In addition to the stepped portion 306 having a coating, at least a portion of the body 302 may also have a coating (generally denoted by 308), which has the purpose of assisting the implant 300 to integrate into the skeletal bone (shown as 310 in FIG. 14).

In one embodiment, the coating is a suitable porous structure which assists in encouraging bone growth into the porous structure, thereby assisting osseointegration of the implant into the skeletal bone. In one embodiment, the porous structure is formed from titanium which is deposited on the surface of the body 302 by using a plasma deposition process.

The implant has a curved shape which is generally visible at area 312, which is arranged to mimic the curve of a human femoral bone. It will be understood that different types of implants may have different shapes and profiles, as may be required to meet certain skeletal and anatomical constraints. Such variations are within the purview of a person skilled in the art.

The body 302 of the implant 300 further includes at least one projection 314 which extends along a portion of the body 302. The projection is arranged to, in use, prevent rotation of the implant relative to the skeletal bone, by providing 'grip' to prevent rotation of the implant 300 when it is located inside the skeletal bone. In the embodiment shown in the Figures, the projection 314 is at least one spline which extends longitudinally along the body of the implant. However, it will be understood that other variations which achieve the same functionality may include the provision of raised patterns (a 'zig-zag' pattern), circumferential ridges, or other simple or complex patterns.

The implant 300 also has a second end 316 which is tapered, to allow the patient to also receive an artificial hip implant (or other implant) which can be attached to the leg implant.

Referring now to FIGS. 15A to 15B there is shown a coupling part which is arranged to cooperate with the implant 300. The coupling part 400 includes a locking slot 402 arranged to lockingly slot into the implant 300. The coupling part also includes a connector engagement boss 404 arranged to connect, either directly or indirectly, with a prosthetic device (not shown), in cooperation with a locking pin channel 406, which is arranged to receive a pin (not shown) to lock the prosthetic (not shown) to the coupling part 400.

Figure 16:
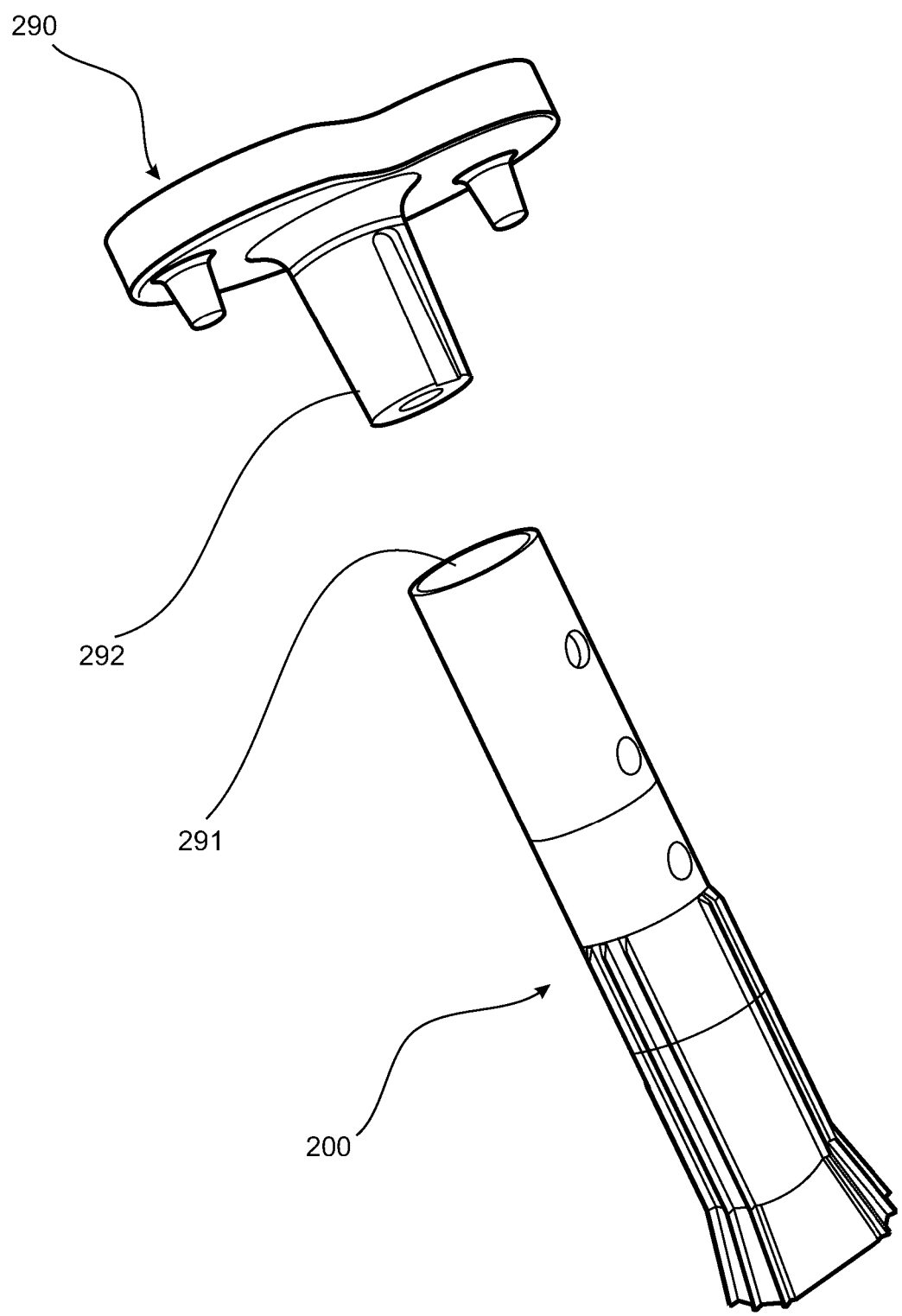
FIG. 16 is a perspective view of an osseointegrative implant in accordance with a fourth embodiment of the present invention.
Figure 17:
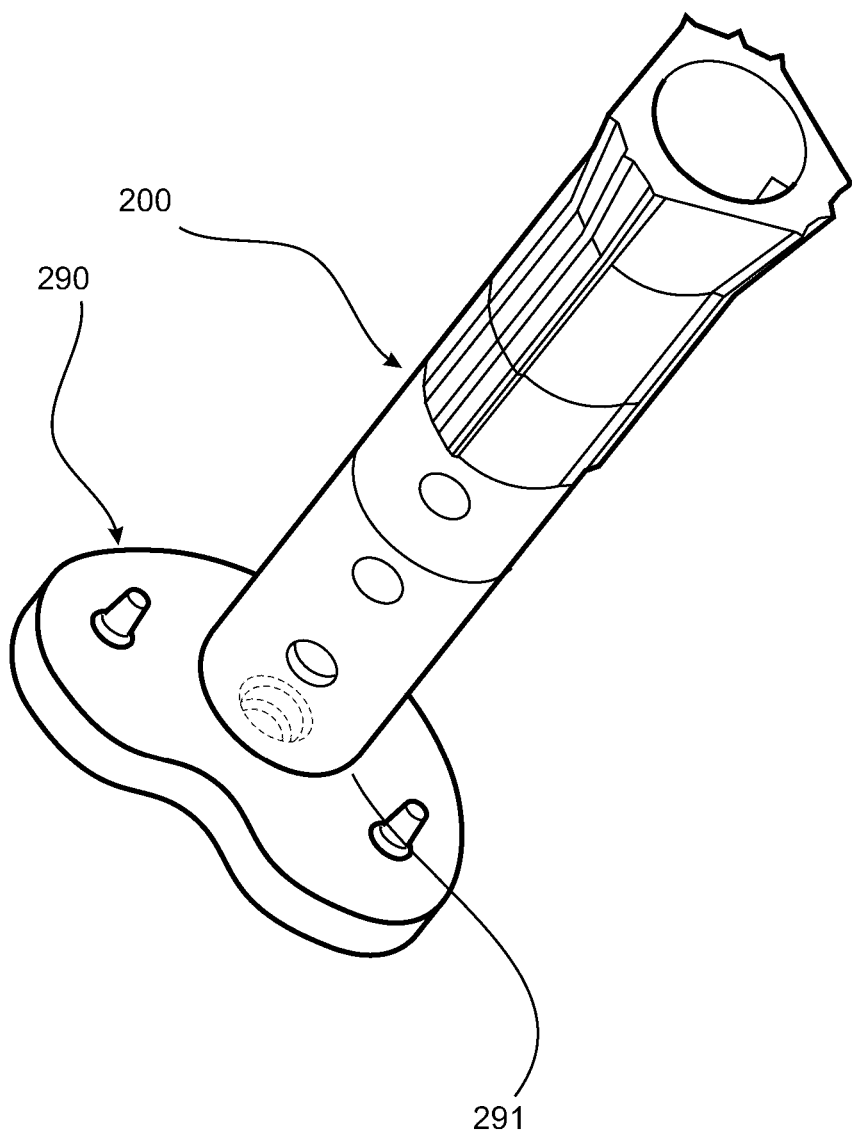
FIG. 17 is a perspective view of the osseointegrative implant of FIG. 16.
Figure 18:
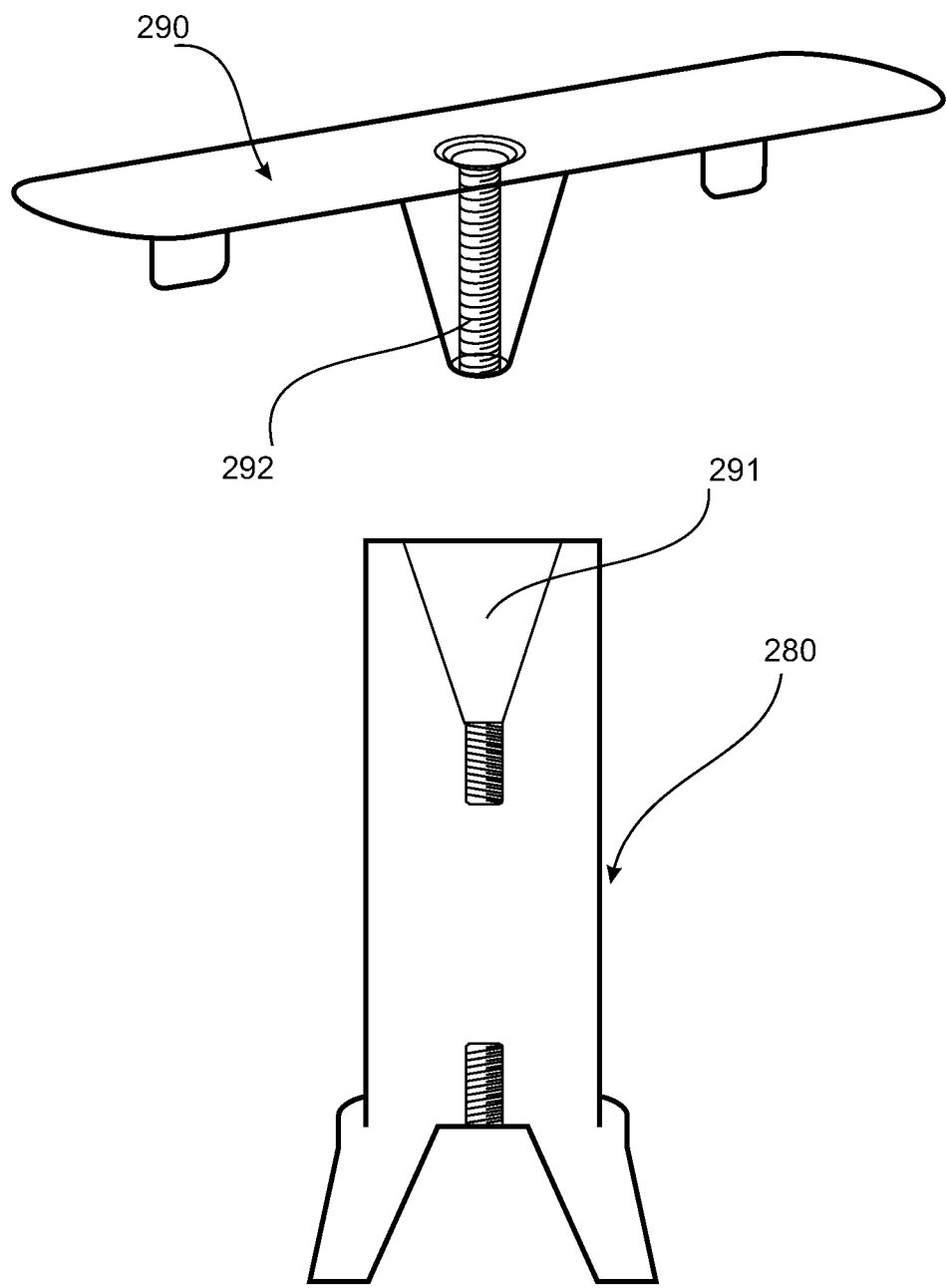
FIG. 18 is a side view of an osseointegrative implant in accordance with a fifth embodiment of the present invention.

Referring now to FIGS. 16, 17 and 18 there is shown a fourth embodiment of the present invention where the osseointegrative implant 200 is attachable to a tibial base plate 290. The tibial base plate 290 is used in a knee replacement. The proximal end 216 of the osseointegrative implant 200 is tapered and includes receiving recess 291 arranged to receive a protrusion 292 in the tibial base plate 290. When the protrusion 292 is received in the receiving recess 291 the two can be fixed together at fixing points 293 and 294 through the use of screws, bolts or other fixing means as would be understood by the skilled addressee. FIG. 18 is an extension 280 to the osseointegrative implant 200.

Although FIGS. 16, 17 and 18 have been described with reference to a knee replacement and tibial osseointergrative implant, the skilled addressee will recognize that this would apply to other joint replacements where a base plate is used.

Figure 19:
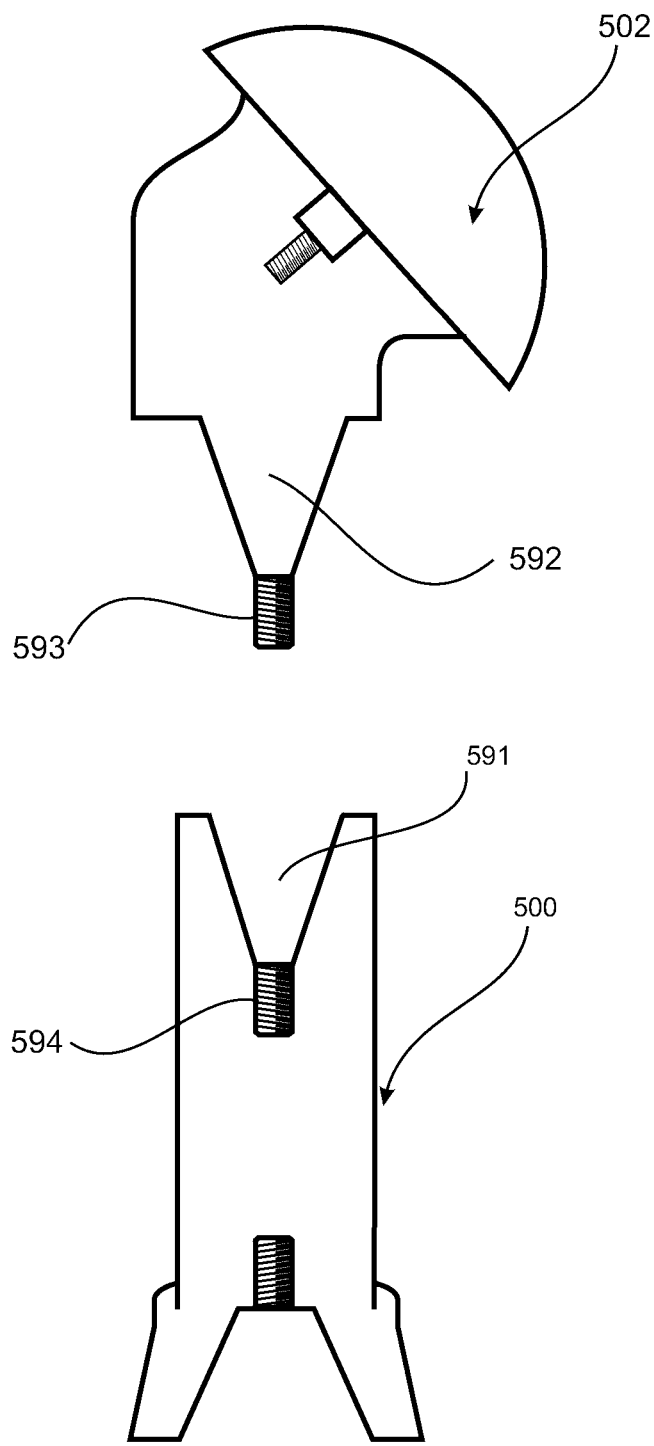
FIG. 19 is a side view of an osseointegrative implant in accordance with a sixth embodiment of the present invention.

Referring now to FIG. 19 there is shown a fifth embodiment of the present invention where a humeral osseointegrative implant not shown is attachable to humeral head replacement 502. The humeral osseointegrative implant includes the features of the osseointegrative implant 100 discussed above. The humeral osseointegrative implant includes and extension 500 with the exception that the proximal end 516 includes a receiving recess 591. The humeral head replacement 502 includes a protrusion 592 arranged to be inserted into the receiving recess 591 of the extension 500. When the protrusion 592 is received in the receiving recess 591 the two can be fixed together at fixing points 593 and 594 through the use of screws, bolts or other fixing means as would be understood by the skilled addressee.

Figure 20:
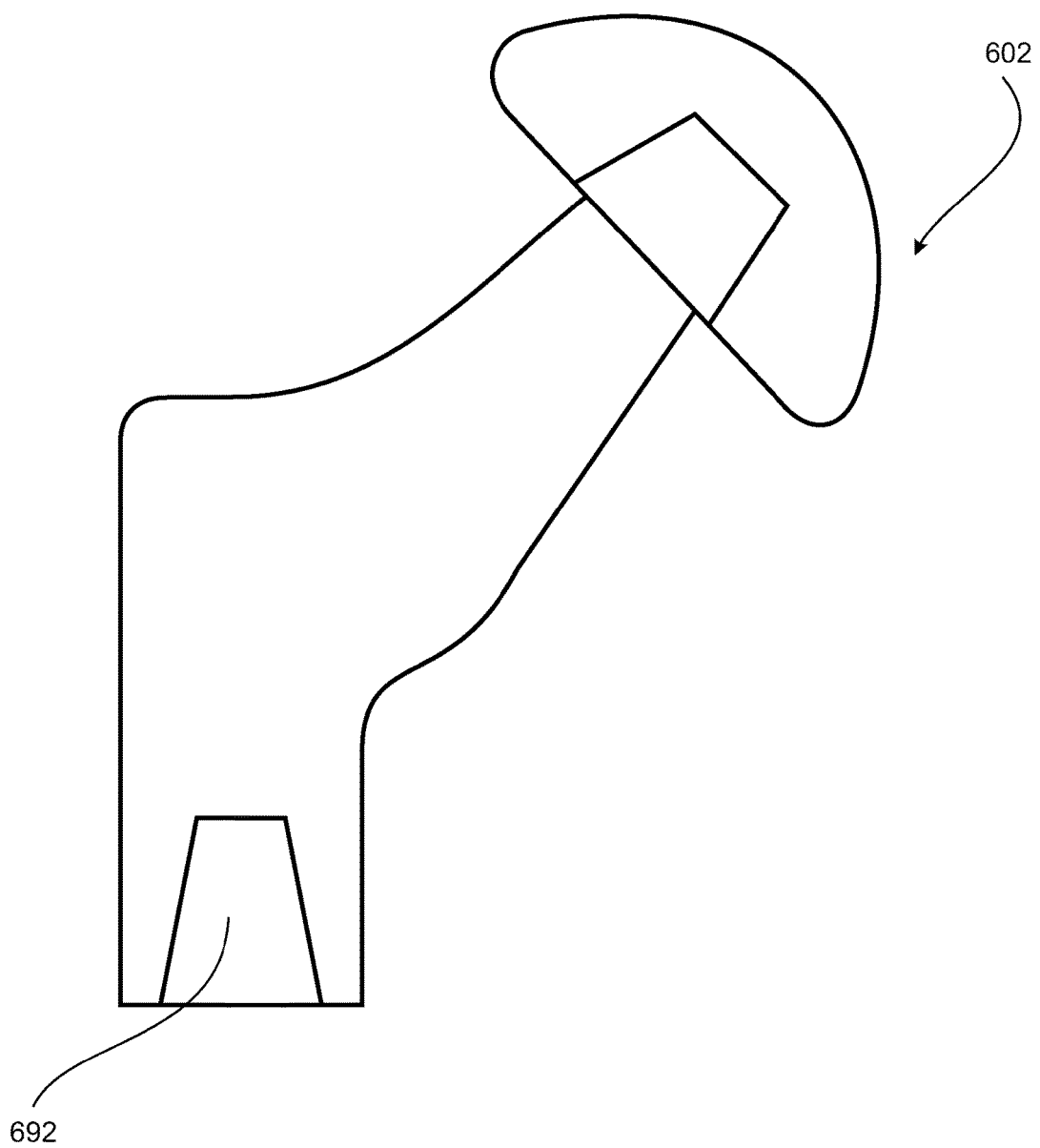
FIG. 20 is a side view of a receiving portion for a part of the osseointegrative implant of FIG. 19.

Referring now to FIG. 20 there is shown a sixth embodiment of the present invention where a hip replacement 602 is arranged to be attachable to the osseointegrative implant 100 when used in a femur. The hip replacement 602 includes a recess 692 arranged to receive the proximal end 116 of the osseointegrative implant 100. When the proximal end 116 is received in the recess 691 the two can be fixed together through the use of screws, bolts or other fixing means as would be understood by the skilled addressee.

Figure 21:
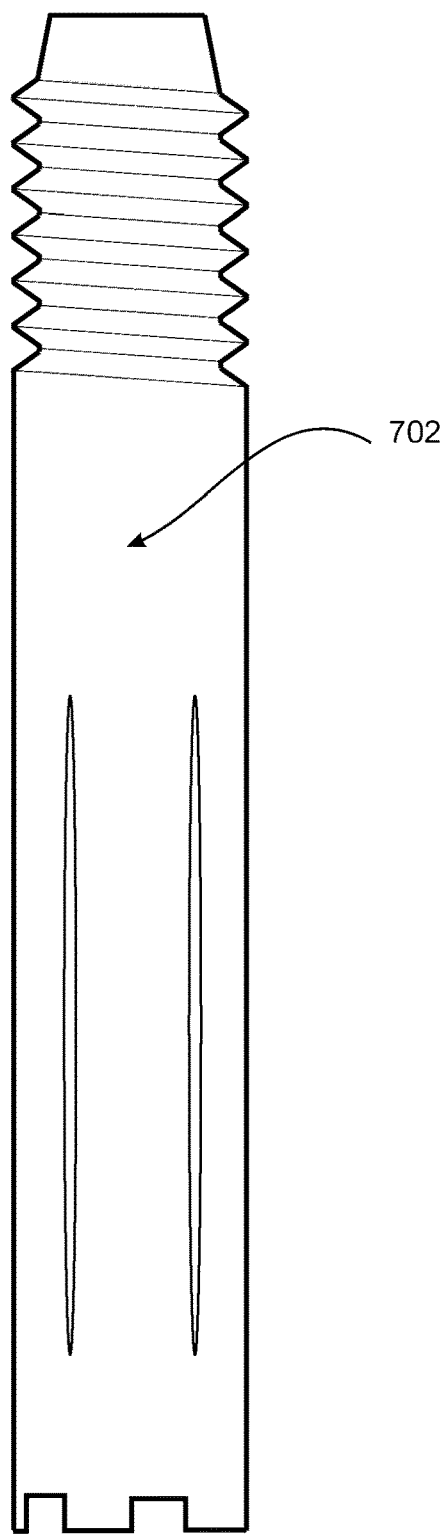
FIG. 21 is a side view of a section of an extension for use with the osseointegrative implant of FIG. 19.
Figure 22:
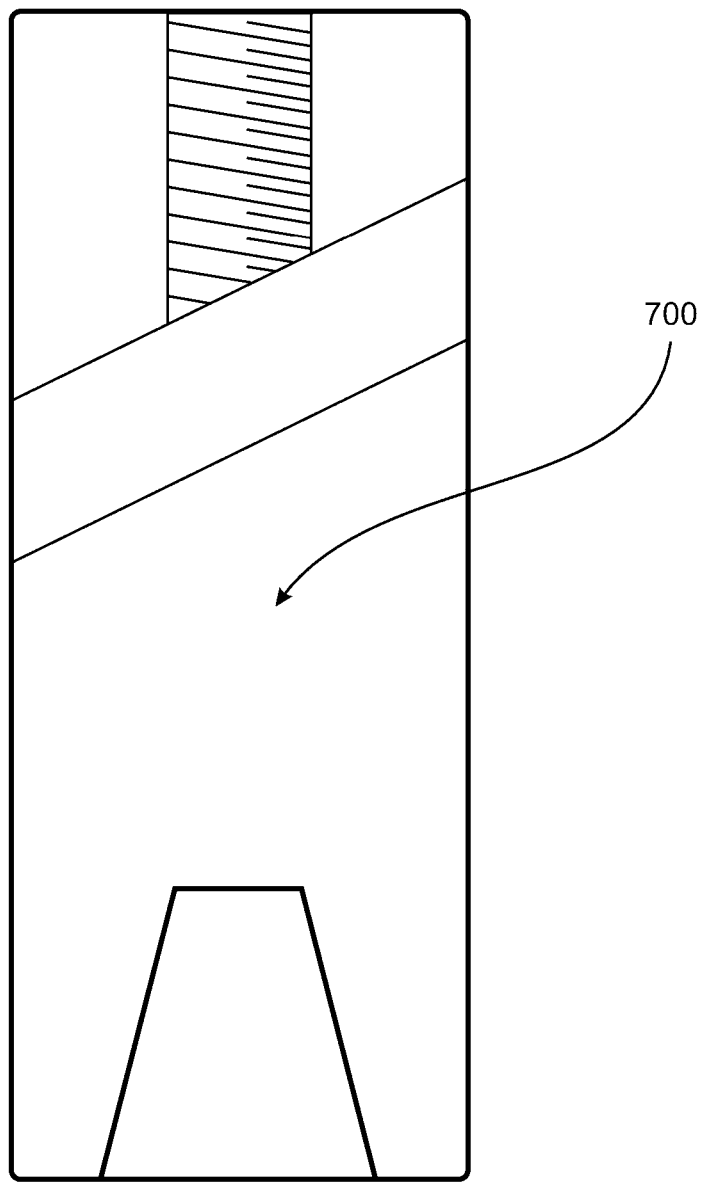
FIG. 22 is a side view of a section of an extension for use with the osseointegrative implant of FIG. 19.

FIG. 21 shows a body screw extension portion 702. FIG. 22 shows a body portion 700 that includes recess 701 to receive the extension portion 702. Extension portion 702 passes through the body portion to screw into the skeletal bone acting as an anchor for the osseointegrative implant 100, 200.

Figure 23:
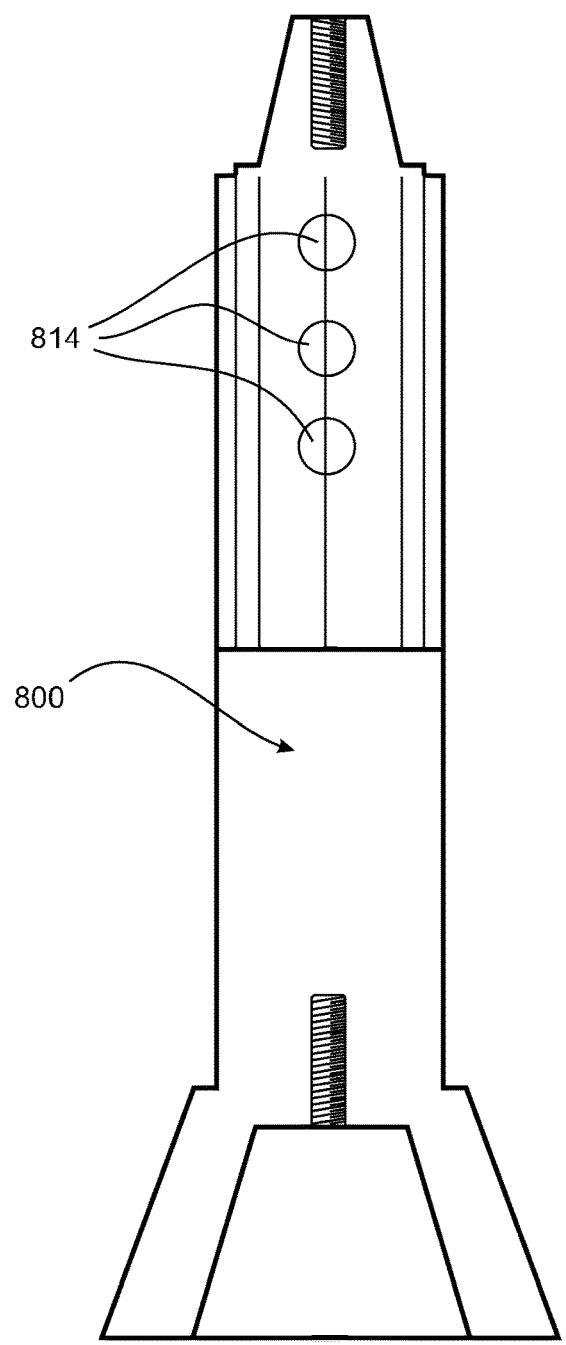
FIG. 23 is a side view of an osseointegrative implant in accordance with a sixth embodiment of the present invention.

FIG. 23 illustrates a seventh embodiment of the present invention with an osseointegrative implant 800 similar to that of osseointegrative implant 100 with fixing points 814. Fixing points 814 operate in the same manner as fixing points 214, but are located at the proximal rather than distal end.

Figure 24:
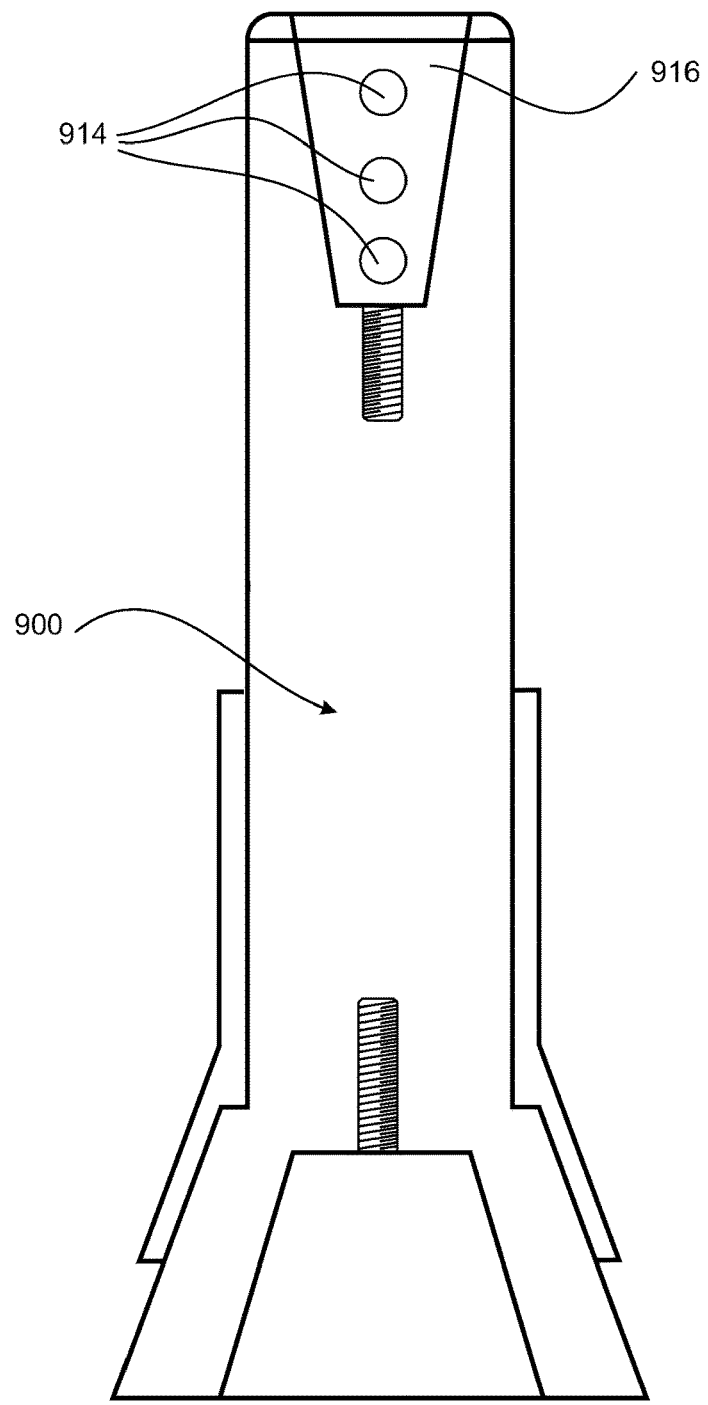
FIG. 24 is a side view of an osseointegrative implant in accordance with a sixth embodiment of the present invention.

FIG. 24 illustrates an eighth embodiment of the present invention with an osseointegrative implant 900 similar to that of osseointegrative implant 200 with fixing points 914. Fixing points 914 operate in the same manner as fixing points 214, but are located at the proximal rather than distal end and receiving portion 916 being a profiled recess.

Of course, it will be understood that the osseointegrative implant may be manufactured in different sizes, so that the correct size may be provided for different patients of different heights, weights and builds. This may include manufacturing implants of different lengths and/or implants which have different radial profiles. Such variations are encompassed by the broader inventive concept described and defined herein.

ADVANTAGES AND INDUSTRIAL APPLICABILITY

One of the advantages of the embodiments and broader invention described herein is that the invention flared distal end to stop upward migration of the implant into the flesh of the patient.

Moreover, the embodiment described herein provides longitudinal splines which prevent rotation of the implant.

The implant also preferably includes a porous coating, such as a plasma titanium spray, which acts to induce and assist osseointegration.

Lastly, the embodiment is tapered on the proximal end to allow for future hip/neck implants that may be required by the patient.

DISCLAIMERS

Throughout this specification, unless the context requires otherwise, the word "comprise" or variations such as "comprises" or "comprising", will be understood to imply the inclusion of a stated integer or group of integers but not the exclusion of any other integer or group of integers.

Those skilled in the art will appreciate that the invention described herein is susceptible to variations and modifications other than those specifically described. The invention includes all such variation and modifications. The invention also includes all of the features referred to or indicated in the specification, individually or collectively and any and all combinations or any two or more of the steps or features.

Other definitions for selected terms used herein may be found within the detailed description of the invention and apply throughout. Unless otherwise defined, all other scientific, medical, engineering and technical terms used herein have the same meaning as commonly understood to one of ordinary skill in the art to which the invention belongs.

The invention claimed is:

1. An osseointegration implant arranged, in use, for integration into a skeletal bone of a patient where part of the skeletal bone is missing, comprising:
 a body and at least one end, the body being arranged, in use to sit within a passageway formed within the bone and substantially mimic a portion of a skeletal bone;
 wherein the at least one end includes an enlarged portion arranged to, in use, prevent migration of the implant into the skeletal bone of a patient; and
 wherein the enlarged portion is arranged, in use, to sit within a recess formed in an end of the skeletal bone;
 wherein the recess is connected to the passageway and is of a larger diameter of the passageway;
 wherein the at least one end including the enlarged portion is arranged so that, in use, the end is flush with the end of the skeletal bone; and
 wherein the at least one end is configured as an attachment point for a prosthetic limb.

2. An osseointegration implant in accordance with claim 1, wherein a width of the enlarged portion is narrower than a width of the skeletal bone so that the enlarged portion sits entirely within the recess formed in an end of the skeletal bone when in use.

3. An osseointegration implant in accordance with claim 1, wherein the enlarged portion is tapered away from the body.

4. An osseointegration implant in accordance with claim 1, wherein the enlarge portion is flared away from the body.

5. An osseointegration implant in accordance with claim 1, wherein the body includes a coating arranged, in use, to assist osseointegration of the implant into the existing skeletal bone.

6. An osseointegration implant in accordance with claim 5, wherein the coating includes a porous structure arranged, in use, to assist osseointegration of the implant into the existing skeletal bone.

7. An osseointegration implant in accordance with claim 6, wherein the porous structure is formed from titanium.

8. An osseointegration implant in accordance with claim 7, wherein the porous structure is formed by a plasma deposition process.

9. An osseointegration implant in accordance with claim 1, wherein the implant is sized to be integrated into a human femoral bone.

10. An osseointegration implant in accordance with claim 1, wherein the body of the implant has a curved shape, arranged, in use, to mimic the curve of a human femoral bone.

11. An osseointegration implant in accordance with claim 1, wherein the implant is sized to be integrated into a portion of a human tibial bone.

12. An osseointegration implant in accordance with claim 1, wherein the body of the implant has a curved shape, arranged to mimic the curve of a human tibial bone.

13. An osseointegration implant in accordance with claim 1, wherein the body of the implant further includes at least one projection which extends along a portion of the body, wherein the projection is arranged, in use, to, in use, prevent rotation of the implant relative to the skeletal bone.

14. An osseointegration implant in accordance with claim 13, wherein the projection is at least one spline.

15. An osseointegration implant in accordance with claim 14, wherein the at least one spline extends longitudinally along the body of the implant.

16. An osseointegration implant in accordance with claim 13, including a plurality of splines, wherein a recessed channel is located between adjacent splines.

17. An osseointegration implant in accordance with claim 1, further including a second end, wherein the second end is tapered.

18. An osseointegration implant in accordance with claim 1, wherein a portion of the at least one end is coated with a physiologically inert substance.

19. An osseointegration implant in accordance with claim 1, wherein the body includes an aperture distal to the enlarged portion arranged to receive a locking means arranged to fix the body to the skeletal bone.

20. An osseointegration implant arranged, in use, for integration into a skeletal bone of a patient, comprising:
 a body and at least one end, the body being arranged, in use to sit within a passageway formed within the bone and substantially mimic a portion of a skeletal bone;
 wherein the at least one end includes an enlarged portion arranged to, in use, prevent migration of the implant into the skeletal bone of a patient; and
 wherein the enlarged portion is arranged, in use, to sit within a recess formed in an end of the skeletal bone;
 wherein the recess is connected to the passageway and is of a larger diameter than the passageway; and
 wherein the at least one end is configured as an attachment point for a prosthetic limb.

* * * * *

UNITED STATES PATENT AND TRADEMARK OFFICE
CERTIFICATE OF CORRECTION

PATENT NO. : 10,456,178 B2
APPLICATION NO. : 15/110608
DATED : October 29, 2019
INVENTOR(S) : Munjed Al Muderis Page 1 of 2

It is certified that error appears in the above-identified patent and that said Letters Patent is hereby corrected as shown below:

In the Drawings

Figure 7:
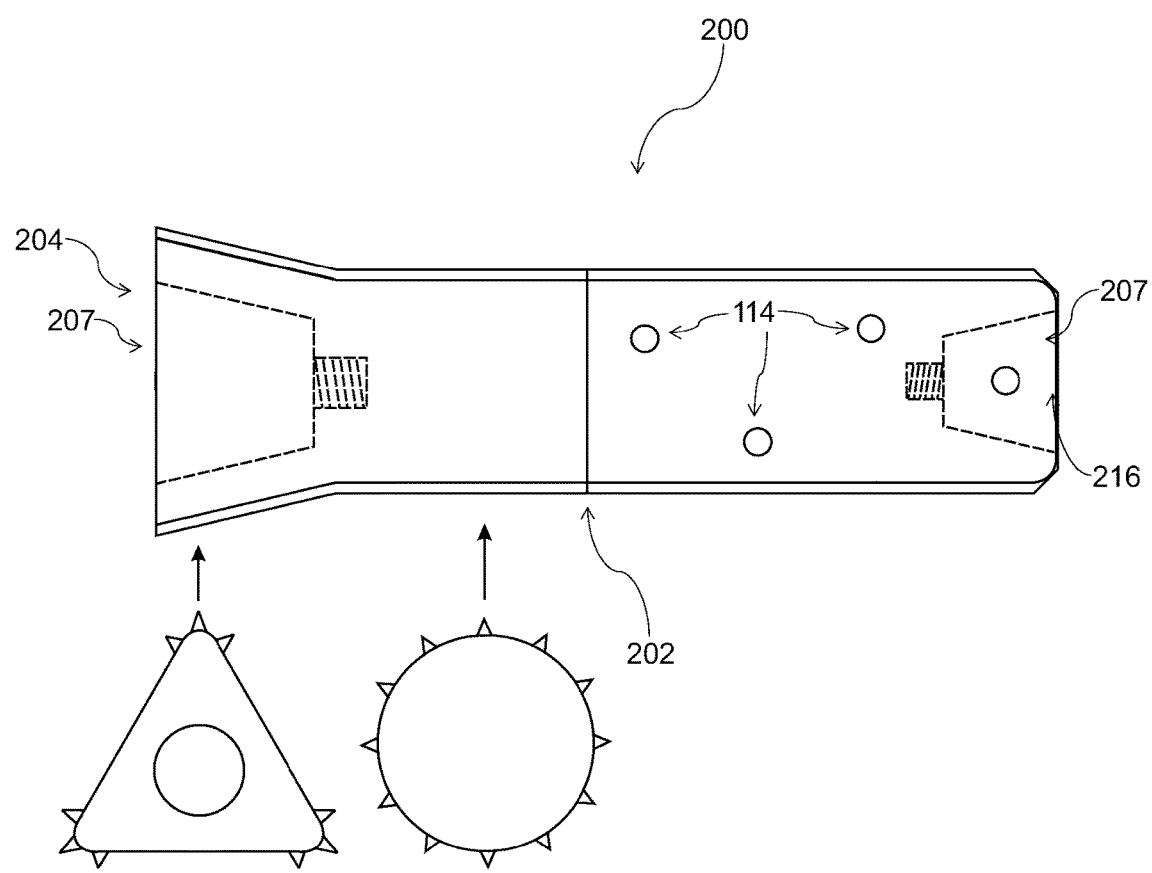
FIG. 7 is a side view of an implant device in accordance with a second embodiment of the present invention.
Figure 8:
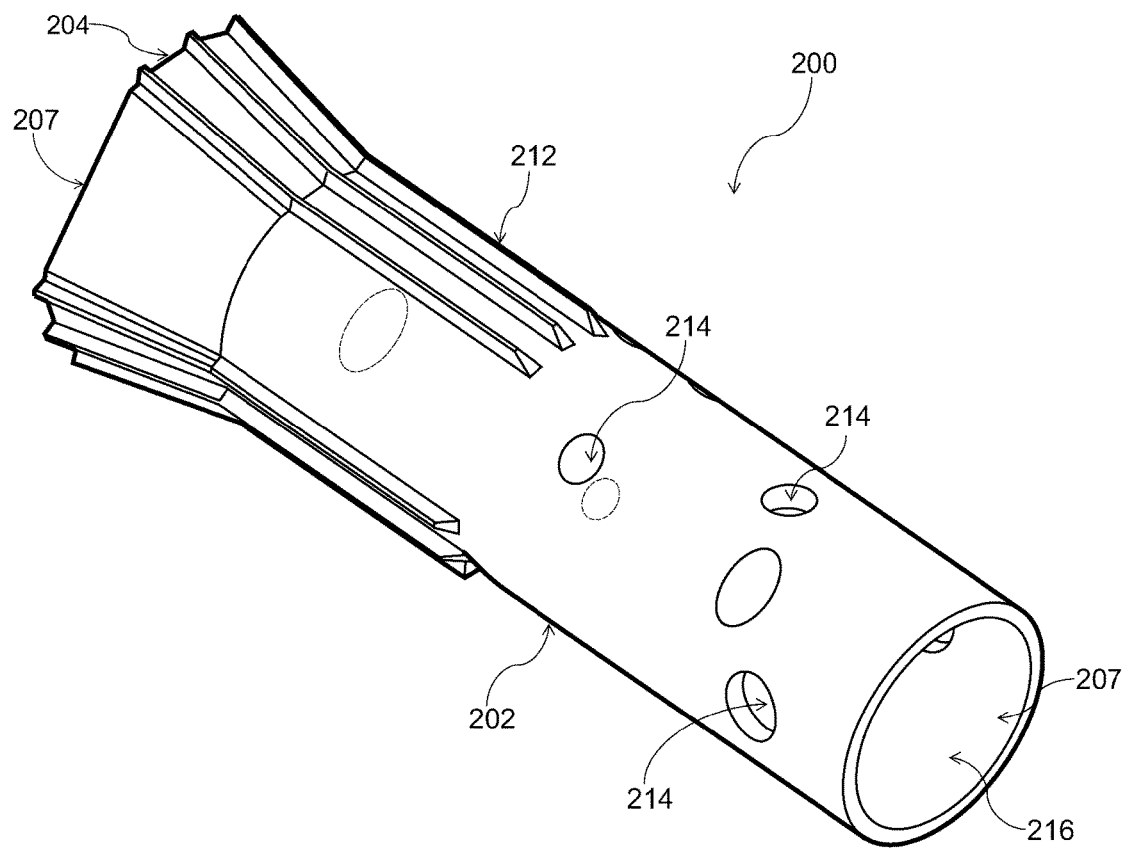
FIG. 8 is a projected view of the implant device of FIG. 7.
Figure 9:
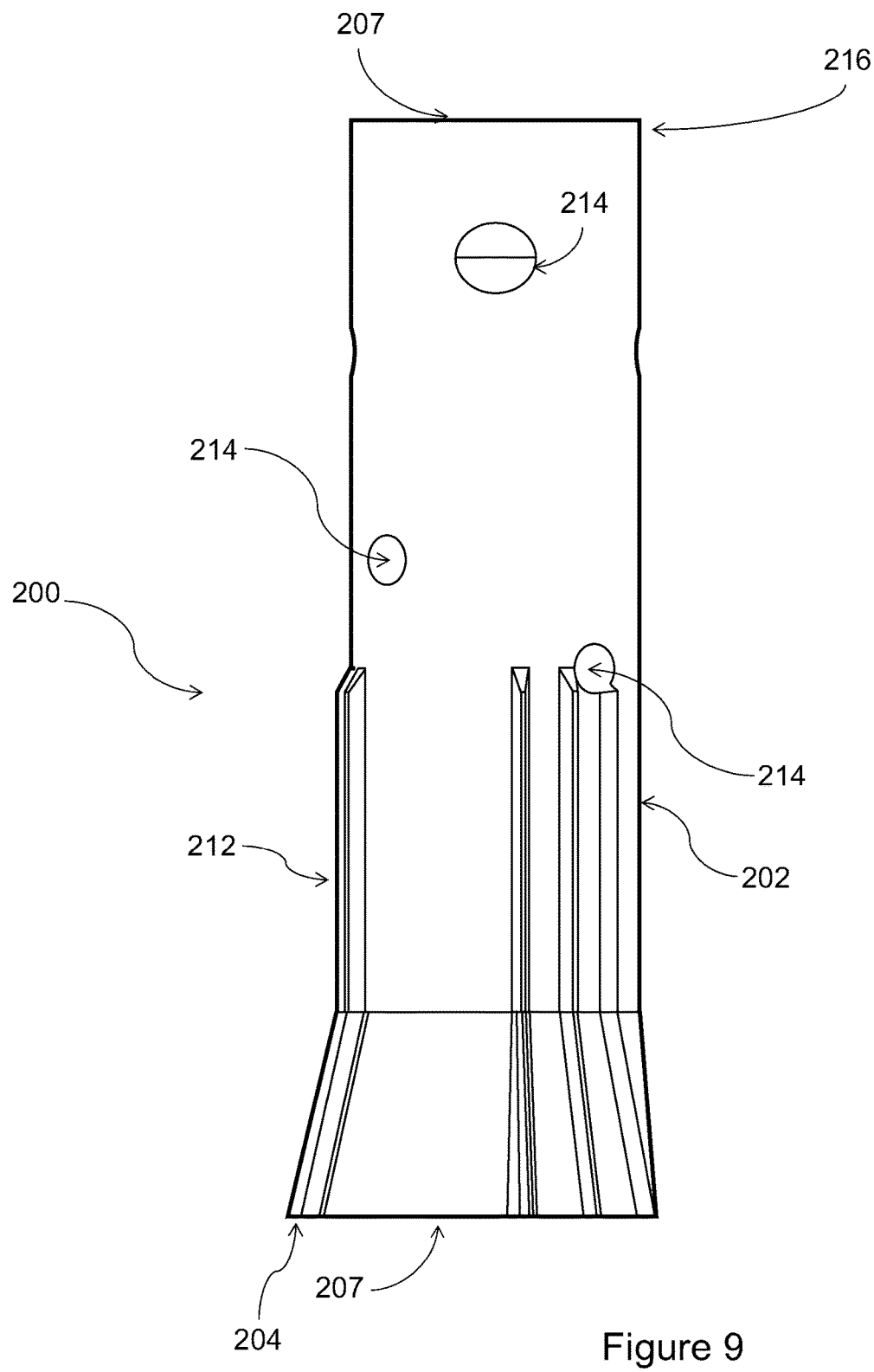
FIG. 9 is a side view of the implant device of FIG. 7, when implanted in a tibial bone.
Figure 10:
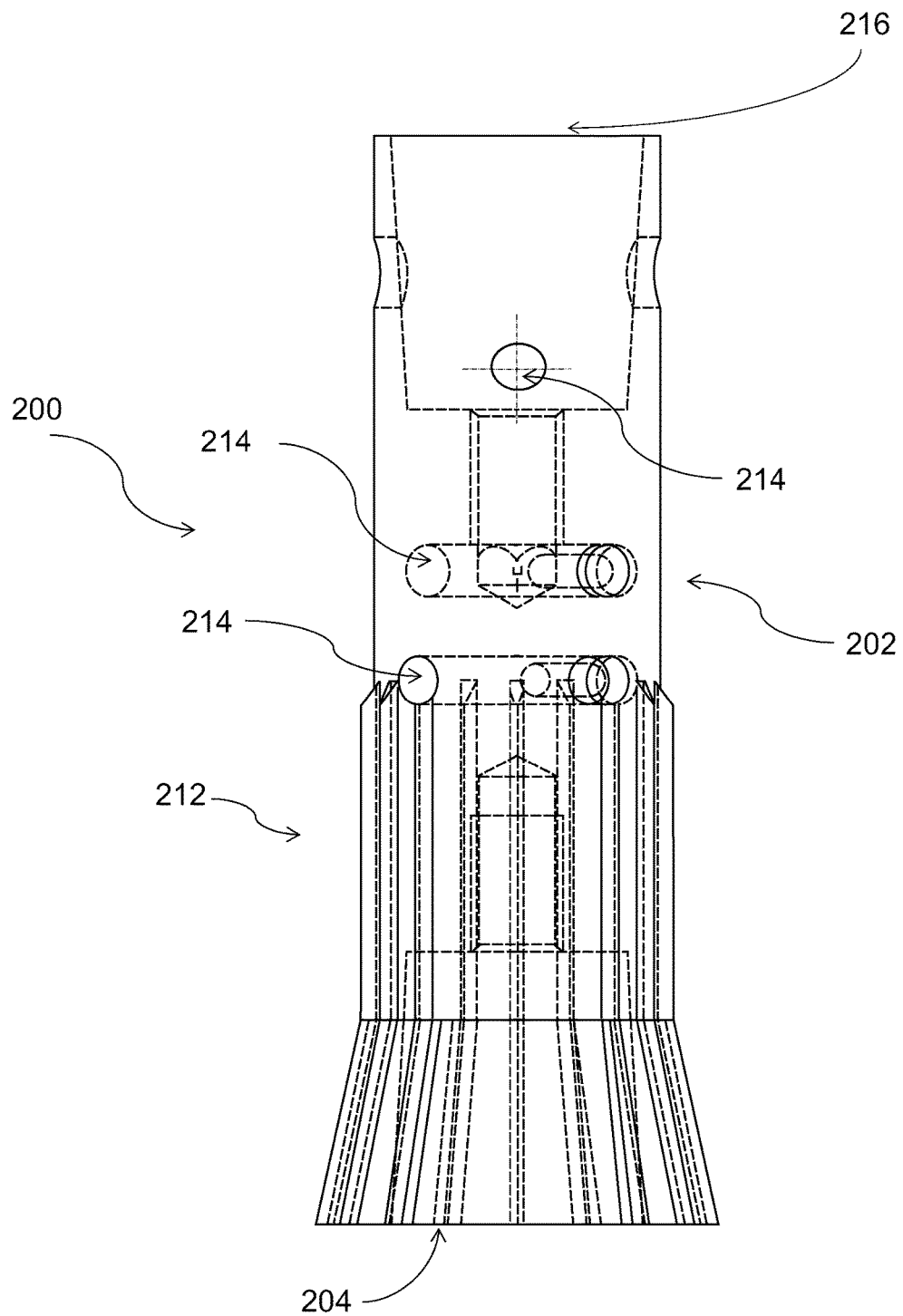
FIG. 10 is a top view of the implant device of FIG. 7 at the other end with a prosthetic.

Sheet 7 of 25, Reference Numeral 207, (First Occurrence), Fig. 7, Delete "207" and insert --206-- therefor Sheet 8 of 25, Reference Numeral 207, (First Occurrence), Fig. 8, Delete "207" and insert --206-- therefor Sheet 9 of 25, Reference Numeral 207, (Second Occurrence), Fig. 9, Delete "207" and insert --206-- therefor Sheet 12 of 25, Reference Numeral 104, Fig. 12, Delete "104" and insert --304-- therefor Sheet 12 of 25, Reference Numeral 106, Fig. 12, Delete "106" and insert --306-- therefor Sheet 12 of 25, Reference Numeral 102, Fig. 12, Delete "102" and insert --302-- therefor Sheet 12 of 25, Reference Numeral 107, Fig. 12, Delete "107" and insert --307-- therefor Sheet 12 of 25, Reference Numeral 116, Fig. 12, Delete "116" and insert --316-- therefor Sheet 12 of 25, Reference Numeral 108, Fig. 12, Delete "108" and insert --308-- therefor Sheet 12 of 25, Reference Numeral 114, Fig. 12, Delete "114" and insert --314-- therefor In the Specification Column 4, Brief Description of the Drawings, Line 8, Delete "15C" and insert --15B-- therefor Column 5, Description of Embodiments, Line 37, Delete "106" and insert --100-- therefor Signed and Sealed this
Twenty-sixth Day of May, 2020

Andrei Iancu
*Director of the United States Patent and Trademark Office*

CERTIFICATE OF CORRECTION (continued)
U.S. Pat. No. 10,456,178 B2

Column 5, Description of Embodiments, Lines 56-58, Delete "FIGS. 15A and 15B are front, and projected views of a first coupling part arranged to couple at one end with the osseointegrative implant of FIG. 12;" and insert --The distal end 104 of the implant 100 further includes a coupling part 107 which is arranged to receive a coupling part (which will be described in more detail later).-- therefor Column 7, Description of Embodiments, Line 24, Delete "106" and insert --206-- therefor Column 7, Description of Embodiments, Line 41, Delete "206" and insert --200-- therefor Column 7, Description of Embodiments, Line 48, Delete "106" and insert --206-- therefor Column 7, Description of Embodiments, Line 59, Delete "214" and insert --212-- therefor Column 7, Description of Embodiments, Line 63, Delete "'zig zag'" and insert --'zig-zag'-- therefor Column 8, Description of Embodiments, Line 21, Delete "6c" and insert --6C-- therefor In the Claims Column 11, Line 35, In Claim 4, delete "enlarge" and insert --enlarged-- therefor Column 12, Line 14, In Claim 13, delete "to, in use," and insert --to-- therefor